United States Patent
Mark et al.

(10) Patent No.: US 10,383,680 B2
(45) Date of Patent: *Aug. 20, 2019

(54) BI-POLAR SURGICAL INSTRUMENT

(71) Applicant: Nico Corporation, Indianapolis, IN (US)

(72) Inventors: Joseph L. Mark, Indianapolis, IN (US); Brian C. Dougherty, Terre Haute, IN (US)

(73) Assignee: Nico Corporation, Indianapolis, IN (US)

( * ) Notice: Subject to any disclaimer, the term of this patent is extended or adjusted under 35 U.S.C. 154(b) by 1030 days.

This patent is subject to a terminal disclaimer.

(21) Appl. No.: 14/639,887

(22) Filed: Mar. 5, 2015

(65) Prior Publication Data
US 2015/0209101 A1     Jul. 30, 2015

Related U.S. Application Data

(63) Continuation-in-part of application No. 13/975,486, filed on Aug. 26, 2013, now Pat. No. 9,782,220, and
(Continued)

(51) Int. Cl.
*A61B 18/14*     (2006.01)
*A61B 18/00*     (2006.01)
*A61B 18/12*     (2006.01)

(52) U.S. Cl.
CPC ........ *A61B 18/148* (2013.01); *A61B 18/1482* (2013.01); *A61B 18/1492* (2013.01);
(Continued)

(58) Field of Classification Search
CPC ... A61B 18/14; A61B 18/148; A61B 18/1482; A61B 18/1492; A61B 2018/00029;
(Continued)

(56) References Cited

U.S. PATENT DOCUMENTS

| 4,590,934 A | 5/1986 | Malis et al. |
| 5,318,563 A | 6/1994 | Malis et al. |

(Continued)

FOREIGN PATENT DOCUMENTS

| EP | 1795139 A1 | 6/2007 |
| JP | 09313496 A | 12/1997 |

(Continued)

OTHER PUBLICATIONS

Lantis et al. Journal of Laparoendoscopic and advanced surgical techniques 1998, vol. 8, No. 6, p. 381-396, "Comparison of Coagulation Modalities in Surgery."

(Continued)

*Primary Examiner* — Linda C Dvorak
*Assistant Examiner* — Khadijeh A Vahdat
(74) *Attorney, Agent, or Firm* — Kristin L. Murphy; Honigman LLP

(57) ABSTRACT

A surgical device is disclosed that comprises a shaft member and a pair of electrodes. The shaft member has a pair of electrode channels that open at the distal end of the shaft member, wherein the electrode channels are positioned adjacent to one another. The pair of electrodes are configured to deliver energy, and one of the pair of electrodes are configured to be disposed in each electrode channel such that distal ends of each of the electrodes are arranged to protrude from the distal end of the shaft member. The shaft member further includes at least one lumen opening at the distal end of the shaft member.

15 Claims, 21 Drawing Sheets

Related U.S. Application Data a continuation-in-part of application No. 13/975,494, filed on Aug. 26, 2013, now Pat. No. 9,775,672.

(60) Provisional application No. 61/695,411, filed on Aug. 31, 2012.

(52) U.S. Cl.
CPC ............ *A61B 2018/00029* (2013.01); *A61B 2018/00035* (2013.01); *A61B 2018/00166* (2013.01); *A61B 2018/00339* (2013.01); *A61B 2018/00404* (2013.01); *A61B 2018/00589* (2013.01); *A61B 2018/00595* (2013.01); *A61B 2018/00946* (2013.01); *A61B 2018/126* (2013.01); *A61B 2018/1422* (2013.01); *A61B 2018/1465* (2013.01); *A61B 2218/002* (2013.01); *A61B 2218/007* (2013.01)

(58) Field of Classification Search
CPC .......... A61B 2018/00035; A61B 2018/00166; A61B 2018/00339; A61B 2018/00404; A61B 2018/00589; A61B 2018/00898; A61B 2018/00946; A61B 2018/126; A61B 2018/1422; A61B 2018/1465; A61B 2218/002; A61B 2218/007
USPC .................................................. 606/28–52
See application file for complete search history.

(56) References Cited

U.S. PATENT DOCUMENTS

| | | | |
|---|---|---|---|
| 5,458,597 A * | 10/1995 | Edwards | A61B 18/1477 604/21 |
| 5,571,100 A | 11/1996 | Goble et al. | |
| 5,873,877 A | 2/1999 | McGaffigan | |
| 5,899,884 A | 5/1999 | Cover | |
| 6,379,351 B1 | 4/2002 | Thapliyal | |
| 6,730,081 B1 | 5/2004 | Desai | |
| 7,645,277 B2 | 1/2010 | McClurken et al. | |
| 2001/0014806 A1 | 8/2001 | Ellman et al. | |
| 2002/0077590 A1 * | 6/2002 | Ponzi | A61B 18/1492 604/95.01 |
| 2003/0216690 A1 * | 11/2003 | Foley | A61M 1/0047 604/119 |
| 2005/0245923 A1 | 11/2005 | Christopherson | |
| 2011/0022047 A1 | 1/2011 | Buysse et al. | |
| 2011/0178515 A1 | 7/2011 | Bloom et al. | |
| 2012/0123410 A1 * | 5/2012 | Craig | A61B 42/10 606/41 |
| 2013/0066317 A1 | 3/2013 | Evans et al. | |
| 2013/0331833 A1 | 12/2013 | Bloom | |
| 2016/0015451 A1 | 1/2016 | Shikhman | |

FOREIGN PATENT DOCUMENTS

| | | |
|---|---|---|
| JP | 10127658 A | 5/1998 |
| JP | 11226024 A | 8/1999 |
| JP | 2002028166 A | 1/2002 |
| WO | 9909919 A1 | 3/1999 |
| WO | 2013038042 A1 | 3/2013 |

OTHER PUBLICATIONS

Scarff., Surg. Neufol. May 1974, vol. 2, p. 213, "A New Bipolar Suction-Cautery Forceps for Micro-Neurosurgical Use."

Donzelli et al. Otolaryngology—Head and Neck Surgery Sep. 1998, vol. 119, No. 3, p. 153-158, "Thermoprotective mechanisms of irrifation during bipolar cautery."

King et al. J. Neurosurg. Aug. 1972, vol. 37, p. 246-247, "Self-irrigating bipolar diathermy forceps, Technical Note."

Sharma et al. Indian J. Plast. Surg, Jul.-Dec. 2005. vol. 41, Issue 2, p. 162-166, "Irrigation-coupled bipolar cautery unit: A practical, economical, and simple version."

O'Connor et al. Surgery Apr. 1996, vol. 119, No. 4, p. 390-396, "William T. Bovie and electrosurgery."

Dujovny et al. Plastic and Reconstructive Surgery Nov. 1975, vol. 56, No. 5, p. 585-587, "Bipolar Jeweler's Forceps With Automatic Irrigation, for Coagulation in Microsurgery."

Nakagawa et al. Circulation 1995, vol. 91, p. 2264-2273, "Comparison of in Vivo Tissue Temperature Profile and Lesion Geometry for Radiofrequency Ablation With a Saline-Irrigated Electrode Versus Temperature Control in a Canine Thigh Muscle Preparation."

Sakatani et al. J. Neurosurg 1995, vol. 82, p. 669-671, "Isotonic mannitol and the prevention of local heat generation and tissue adherence to bipolar diathermy forceps tips during electrical coagulation, Technical Note."

Topp et al. Annals of Surgery Apr. 2004, vol. 239, No. 4, p. 518-527, "Saline-Linked Surface Radiofrequency Ablation Factors Affecting Steam Popping and Depth of Injury in the Pig Liver."

Malis., Operative Neurosurgery Feb. 2006, vol. 58, p. ONS1-ONS12, "Electrosurgery and Bipolar Technology."

PCT International Search Report and Written Opinion dated Dec. 12, 2013 for PCT/US2013/056765.

* cited by examiner

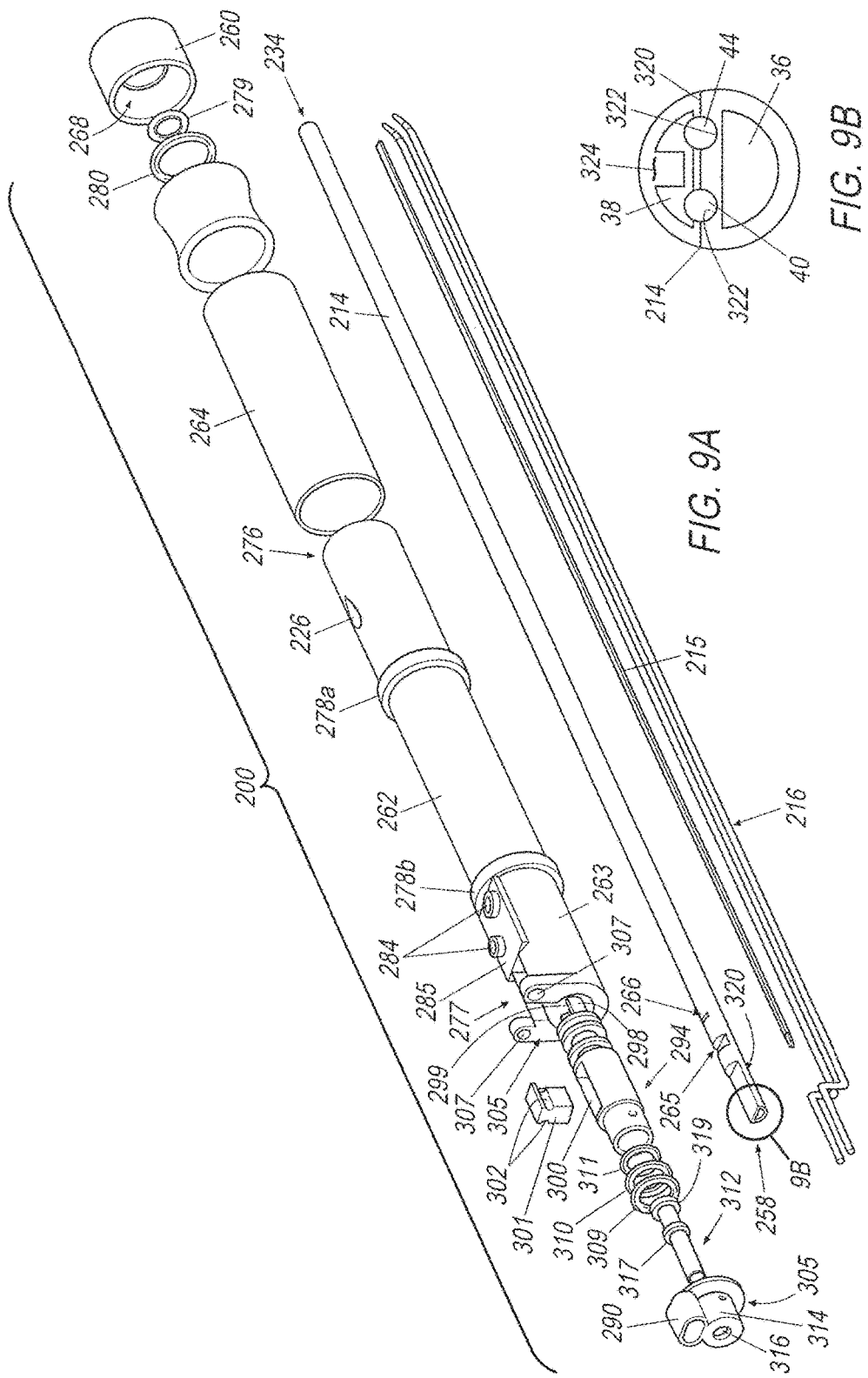

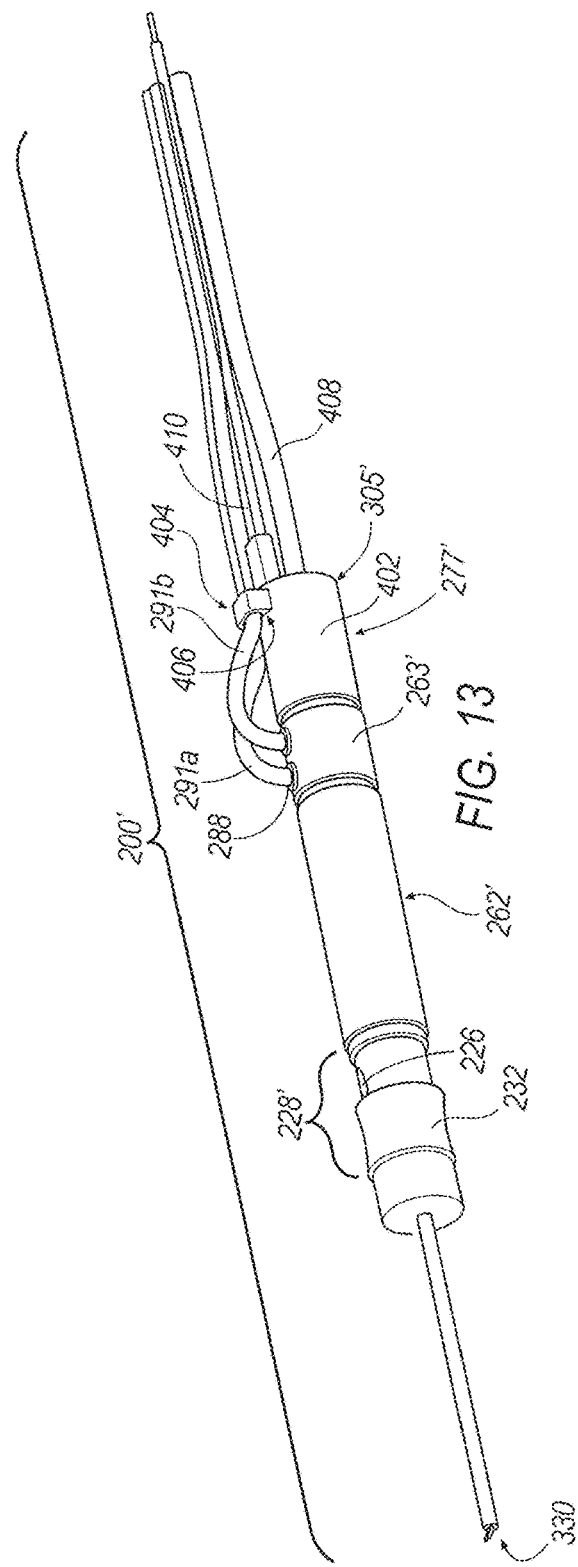

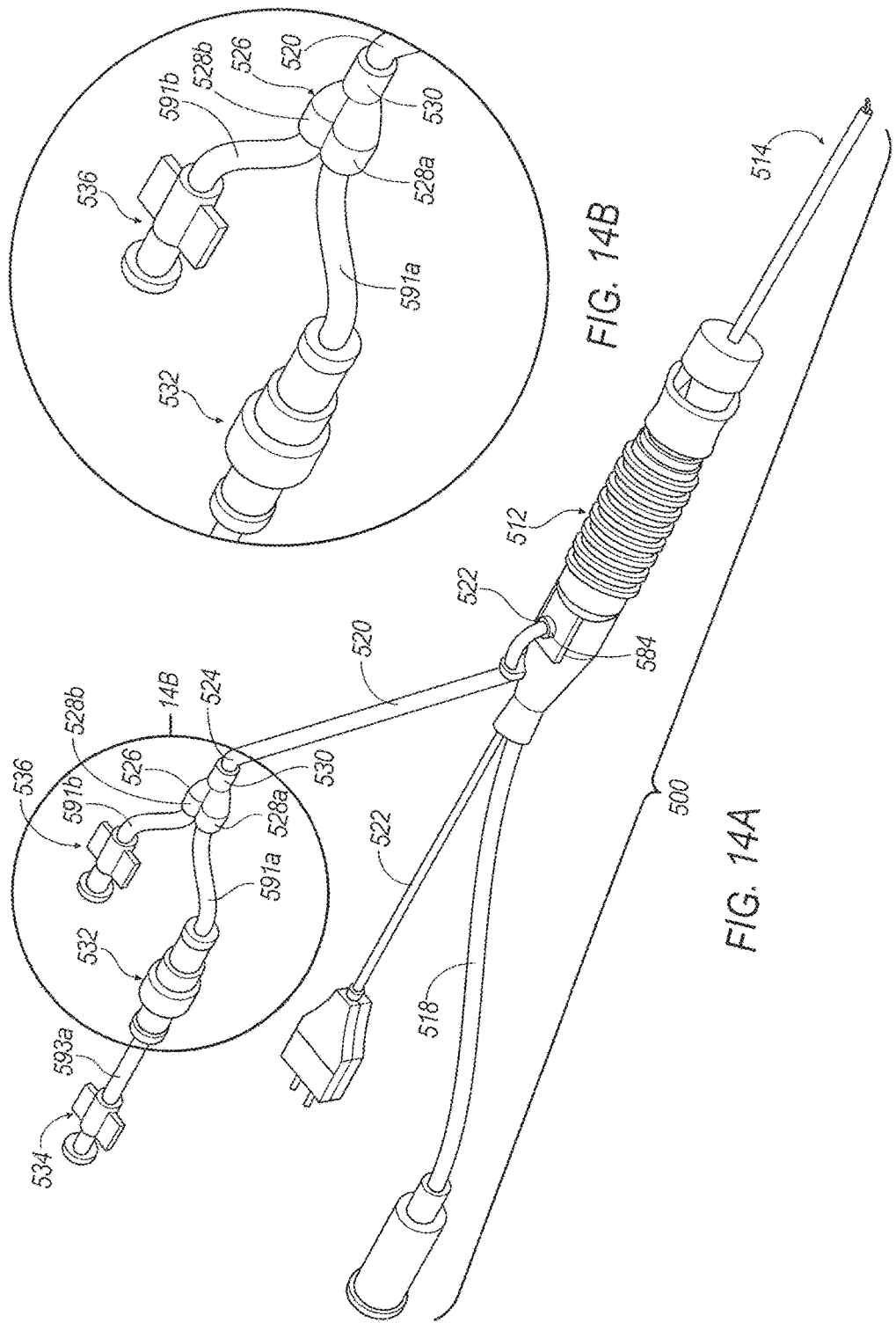

BI-POLAR SURGICAL INSTRUMENT

CROSS-REFERENCE TO RELATED APPLICATIONS

This application is a continuation-in-part application of U.S. Ser. No. 13/975,486, filed on Aug. 26, 2013, Now U.S. Pat. No. 9,782,220 and U.S. Ser. No. 13/975,494, filed on Aug. 26, 2013, Now U.S. Pat. No. 9,775,672, which applications claim priority to U.S. Provisional Patent Application No. 61/695,411, filed Aug. 31, 2012, the disclosures of which is-are incorporated by reference in ifs-their entirety.

TECHNICAL FIELD

The present disclosure relates to surgical devices, in particular, surgical devices that employ a bi-polar surgical device that is suited for microsurgical applications such as neurosurgical and spinal surgical procedures, while minimizing thermal impact to surrounding tissue.

BACKGROUND

Monopolar devices have been employed for years to cauterize vessels and cut tissue depending on the frequency used. Monopolar devices operate by using the patient as the ground pathway to complete the circuit. However, this arrangement is not efficacious in certain applications, such as neurosurgical procedures, as the energy moves through the entire body, including, for example, brain tissue.

Bipolar cautery devices have also been employed to coagulate and cauterize tissues such as vessels. Bipolar cautery devices utilize two electrodes, with the intent to localize energy between the two poles of the electrodes, thereby minimizing energy delivery to adjacent tissues and structures. However, one of the issues with bipolar cautery devices is the ability to control the amount of energy to be delivered to accomplish the desired coagulation or tissue welding, depending on the application. Less energy is required the closer the electrodes are positioned together. However, it is undesirable to have the electrodes contact each other directly, as when this happens, no energy is being delivered to the intended tissues and no coagulation/cautery occurs to the intended tissue. If the electrodes are spaced too far apart, more energy is required to achieve coagulation, which can lead to collateral tissue damage.

In certain applications, such as in neurosurgical applications, it is desirable to deliver as low an amount of energy as possible when attempting to mitigate a bleeding vessel to prevent collateral tissue damage, especially around critical structures within the brain. However, for bipolar cautery devices where the poles are at a fixed distance apart from one another, the amount of energy for a given application can be too great for the intended target, thereby leading to undesirable collateral tissue damage.

In certain instances, carbonization build up occurs on the electrodes due to the heat created at the electrode tip; this carbonization is the result of the tissue being "cooked" onto the surface of the electrode. This buildup compromises the effectiveness of the energy delivery to accomplish coagulation or cauterization on the target tissue. As a result, higher levels of energy are required to be delivered to the electrodes to achieve coagulation of the bleeding vessel to overcome the resistance caused by the buildup. However, the energy levels of the non-buildup areas will then be too high, causing unnecessary thermal damage to surrounding tissues. Moreover, the conductive pathway may also be altered and flow in an unintended pathway, also causing unnecessary thermal damage to surrounding tissues.

It has been proposed to place sealed cooling channels in individual electrodes to reduce the thermal build up at the electrode tip in an attempt to prevent the tissue from being "cooked" on to the surface of the electrode which can lead to thermal damage to collateral tissue. Traditionally, however, these electrodes have a size that is relatively large to accommodate the cooling channels therein, and thus, this size requirement to achieve effective cooling precludes such electrodes from being applied to finer tip electrode designs. Indeed, these large sizes render such arrangements unsuitable for delicate microsurgical procedures, such as, for example, narrow corridor neurosurgical procedures for two reasons (1) the physical size of the electrode tips are too large to delicately handle and manage the vessel and (2) the surgical site is often only a few millimeters of a window to be operated through and the electrode tips preclude visualization of the surgical site.

Another issue that arises with the use of bipolar cautery devices is a phenomenon referred to as "sticktion." Sticktion occurs when, after a vessel is coagulated and the electrodes are moved away from the coagulated/cauterized vessel, part of the vessel "sticks" to the electrodes. This often results in re-opening the vessel due to tearing, causing a rebleed of the vessel. To reduce "sticktion," certain materials, such as silver, platinum, and gold, may be used with the electrodes. Such materials, however, have proven to be of limited effectiveness and of minimal benefit.

One proposed solution to reduce the heat at the electrode tips and thereby reduce tissue buildup, reduce sticktion, as well as minimize thermal damage to collateral tissues, is to provide an external saline drip into the surgical site. However, this approach often requires an additional person in the surgical field to deliver the fluid. Additionally, in minimally invasive microsurgical procedures, the surgical corridor and the subsequent target is relatively small, thus an external drip presents delivery challenges for the additional person and visibility challenges for the surgeon whom is using the coagulation device on the intended tissue to be coagulated due to too many instruments and hands in the surgical field simultaneously thereby precluding visualization at the surgical site. Moreover, it is challenging for the assistant providing the external drip to deliver the fluid to the electrode tips and the necessary location within the surgical site with any accuracy.

Another known bipolar coagulation device is bipolar forceps, whereby the two electrodes may be varied in distance from each other by the user. In some versions of these devices, fluid may be supplied through the forceps' legs of the device. To accommodate delivery of the fluid through the body of the forceps, the device must be relatively large which makes it unsuitable for microsurgical corridor approaches. Additionally, as the fluid delivery is proximal of the electrode tip, instead, this prior art design relies upon the fluid to flow along the body of each of the forceps legs to end up at the surgical site. Often in corridor microsurgical approaches the approach is not in a plane that is conducive to the fluid tracking along the leg of the forceps device. Accordingly, the fluid is not necessarily configured to be simultaneously delivered directly to the electrode tip and the surgical site.

Another issue that occurs in typical procedures using bi-polar devices is the variability of energy delivery at the distal tips due to tissue buildup. More specifically, tissue build-up on the electrode tips changes the resistance within the electrical circuit, i.e., the bipolar device and the attached bipolar generator. As a result, in a typical procedure, a surgeon will need to continually ask a surgical assistant to adjust, i.e, turn up, the output of the coagulation generator so as to compensate for the change in effectiveness of the bipolar device, as the procedure progresses. At some point during the procedure, the ineffectiveness and/or the inability of the bipolar device to deliver energy to effectively coagulate can no longer be accomplished by simple adjustment of the coagulation generator, or the surgeon becomes frustrated with the continuation needed adjustment of the coagulation generator. This frustration results in the surgeon having to remove the bipolar device from the surgical field and have a scrub nurse clean off the electrode tips. Moreover, while the electrode tips are being cleaned, the tissue/vessels that the coagulator was being applied to is still bleeding, causing risk to the patient. Alternatively, if additional bipolar coagulation devices are available, the scrub nurse may remove the bipolar device from the electrical cord attached to the coagulation generator, and replace the bipolar device with another bipolar device. The removal of the bipolar device from the surgical field and either cleaning or swapping it out with another bipolar device goes on repeatedly through an entire procedure.

However, once a surgeon has a clean bipolar device, the surgeon must then have a surgical assistant adjust the output of the coagulation generator again, i.e., turning the output down. As the clean bipolar device is used, the instruction sequence of "turning up and turning down" the output of the coagulation generator and swapping out the bipolar device for either cleaning or for a new bipolar device continues through the entire procedure. This process is inefficient, increases blood loss, which compromises patients' safety, and increases the length of a procedure.

Different vessels are different sizes. Thus, to maximize energy delivery to the intended vessel, it is desirable to straddle as close to the offending vessel as possible to minimize collateral energy dispersion. However, fixed parallel electrodes have no ability to easily accommodate different sized vessels, and often leads to digging into the tissue (and hence thermally damaging collateral tissue) to straddle the vessel.

Currently, bipolar devices also cause line of sight issues, especially during microsurgical procedures which also require working down a narrow corridor. More specifically, the electrode ends of the bipolar of are not visible in conjunction with the area of interest when the device is placed down a corridor, as the electrode shafts and/or the handle of the device or even the user's own hand blocks the view. Bayonet designs have been employed to address the needs of the microscopic procedures but these are of limited effectiveness in narrow corridor microsurgical approaches.

Another issue with currently available bipolar coagulation devices (as well as monopolar devices), is the ability to control visibility within the surgical field to identify an active bleeder and address the bleeder which is of unknown origin. What is needed is a single device which provides the ability to irrigate the entire field to push the blood away from a suspected bleeder location so as the user may clearly see the surgical field so as to locate the bleeder, as well as suction the excess fluid from the surgical field so as to visually clear the field to enable the user to coagulate the offending vessel while minimizing any collateral tissue damage during coagulation/cautery of the vessel.

BRIEF DESCRIPTION OF THE DRAWINGS

Exemplary embodiments of the present disclosure will now be described in greater detail with reference to the attached figures, in which:

FIG. 9A is an exploded view of an alternative arrangement of a bipolar instrument;

FIG. 9B is a proximal end view of a shaft member of the biopolar instrument of FIG. 9A.

FIG. 13 is a perspective view of an assembled bipolar instrument of FIG. 9A with an alternative orientation of a vent aperture and fluid connection.

FIG. 14A is a perspective view of a surgical system with a bipolar instrument operatively connected to a fluid system.

FIG. 14B is an enlarged view of encircled area 14B in FIG. 14A.

DETAILED DESCRIPTION

Figure 1:
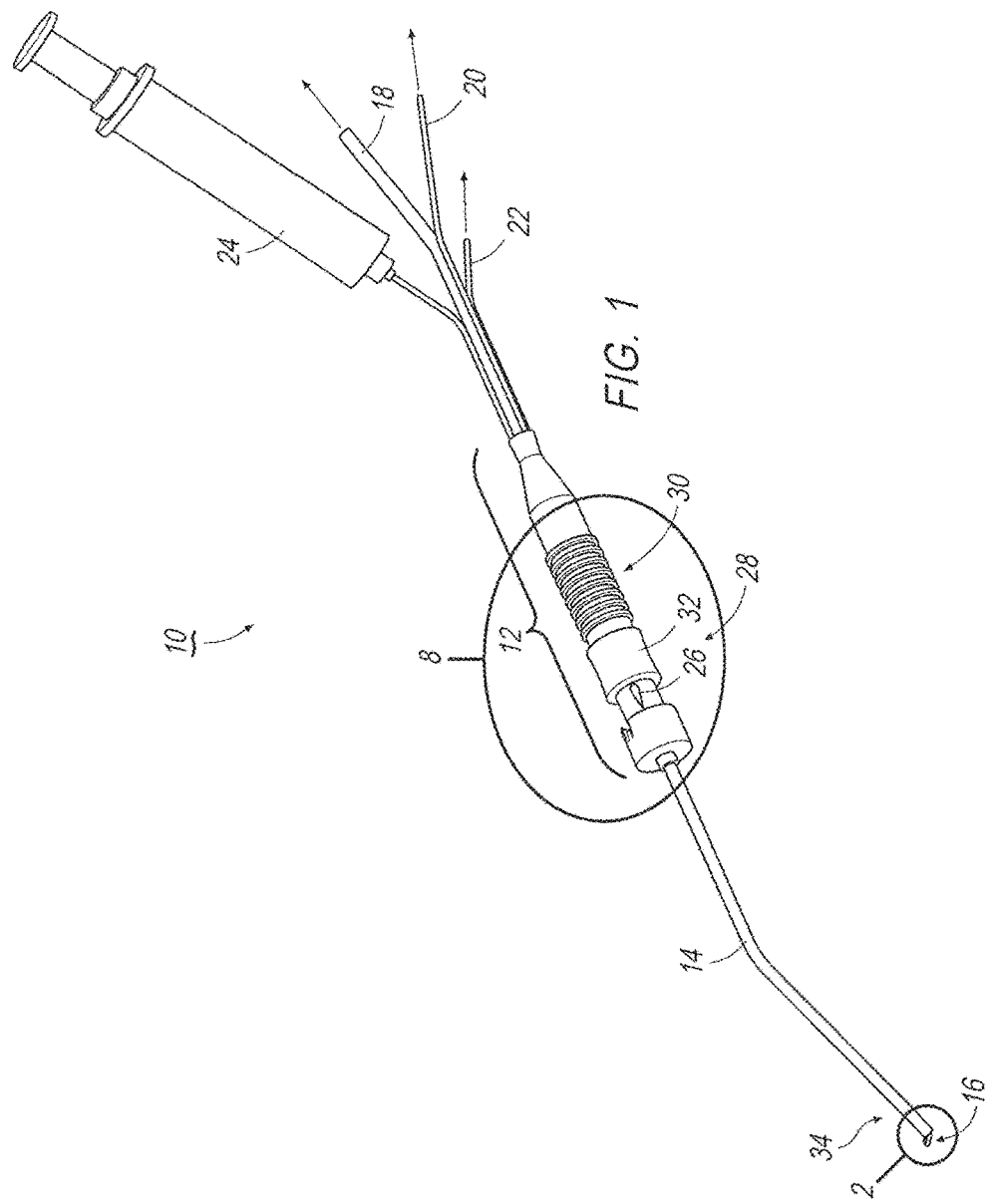
FIG. 1 illustrates a surgical system that includes a bi-polar surgical instrument.

Referring now to the discussion that follows and also to the drawings, illustrative approaches to the disclosed instruments and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is a bipolar coagulation surgical instrument that is configured for aspiration. In addition, an embodiment of the bipolar coagulation surgical instrument also provides for delivery of fluid to the surgical field.

The surgical instrument may be configured to connect to an existing vacuum supply, which may include a vacuum system hose fluidly connected to an existing vacuum source. The vacuum supply may supply a predefined level of vacuum to a distal end of the surgical instrument. The surgical instrument may be configured to include an aspiration control device configured to selectively control the level of vacuum supplied to the distal end, including while in operation in the surgical field.

Figure 2A:
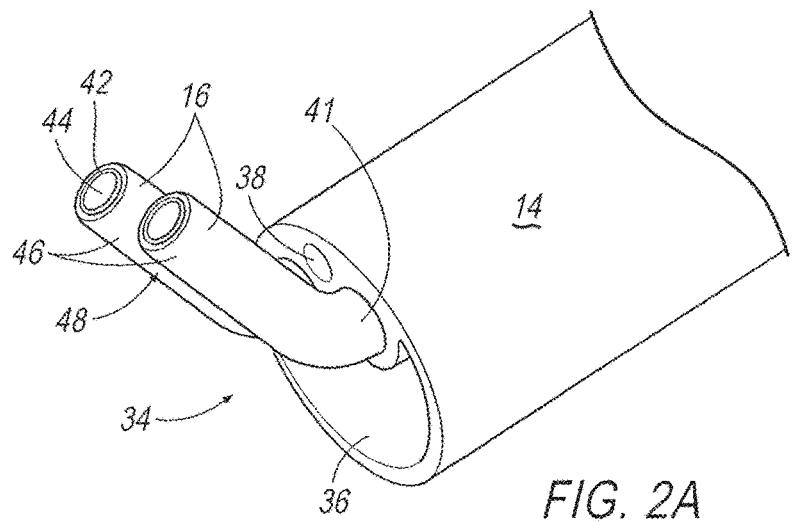
FIG. 2A is an enlarged view of area 2 of FIG. 1 depicting a first exemplary arrangement of a distal end of the bi-polar surgical instrument.

Referring to FIG. 1, a bipolar surgical instrument 10 is illustrated. Surgical instrument 10 comprises a handpiece 12, a shaft member 14 extending distally from handpiece 12 and electrodes 16, 116, 216, 316, 416, 516, 616, 674 as best seen in FIGS. 2A-2N. Operatively connected to handpiece 12 is an aspiration line 18, a fluid delivery line 20, and a cautery supply cable 22. A secondary fluid supply, as exemplified by a syringe 24, may also operatively connected to handpiece 12.

Shaft member 14 may be configured from suitable surgical grade materials so as to be selectively malleable by the user. More specifically, a user may be able to selectively bend shaft member 14 for a selectively customizable surgical instrument 10. However, the material for shaft member 14 must also have a sufficient strength so as to hold its shape once a user bends shaft member 14 to a desired configuration. Examples of suitable surgical grade materials include, but are not limited to stainless steel.

A vent opening 26 may be formed within a portion of handpiece 12. In one exemplary arrangement, vent opening 26 is configured with a teardrop shape. An aspiration pressure control valve 28 may be operatively connected to handpiece 12 to selectively vary the aspiration pressure delivered through shaft member 14, as will be explained in further detail below. In one exemplary arrangement, aspiration pressure control valve 28 is configured as a slidable sleeve 32 that extends around the circumference of a portion of handpiece 12. However, it is understood that other configurations of aspiration pressure control valve 28 are contemplated. More specifically, any configuration of aspiration pressure control valve 28 may be employed so long as aspiration pressure control valve 28 is sized to cover vent opening 26 to provide full aspiration pressure to a distal end 34 of shaft member 14. An outer surface of slidable sleeve 32 may be configured with gripping members (not show) to provide a frictional contact by a user. Similarly, an outer surface of handpiece 12 may also be provided with gripping members 30 to facilitate grasping of handpiece 12.

Turning to FIGS. 2A-2N, various exemplary arrangements of electrodes 16, 116, 216, 316, 416, 516, 616 and 674 and shaft members 14, 514, 614, and 672 will now be discussed. FIG. 2A illustrates distal end 34 of shaft member 14. As may be seen, shaft member 14 includes an aspiration lumen 36 and a fluid lumen 38 that extend therethrough and are open at distal end 34. Electrodes 16 include connection ends 41 that are seated within electrode channels 40 (best seen, for example, in FIG. 3B) and extend distally from a distal end 34 of shaft member 14. In the embodiment shown in FIG. 2A, connection ends 41 of electrodes 16 are sealed within electrode channels 40.

Electrodes 16 each include an irrigation tube 42 disposed therein that defines an irrigation lumen 44 therein that opens at a distal tip 46 of each electrode 16. Irrigation lumens 44 are designed to deliver fluid, such as saline, at a set flow rate. More specifically, the diameter of irrigation lumen 44 may be sized appropriately to deliver fluid at a set flow rate. Irrigation lumens 44 are operatively connected to fluid delivery line 20 within handpiece 12. Fluid delivery line 20 is operatively connected to a fluid supply source such as, for example, saline.

Electrodes 16 are spaced apart from one another to create a treatment pathway 48 therebetween and are angled away from aspiration lumen 36. The angle of electrodes 16 serves to provide increased visibility during use of the surgical instrument 10 as distal tips 46 extend radially outwardly of a periphery of shaft member 14. More specifically, especially in microsurgical corridor approaches, as well as to improve the user's visualization at the surgical site, the distal tips 46 are in a different plane than the shaft member 14, in a "up toe" configuration, thereby allowing a user to see the distal tips 46 while working in the surgical field, even in a narrow corridor. Angled electrodes 16 also allow the user to apply the electrodes in a parallel manner to a surface of the tissue or vessel to be coagulated. As visibility of distal tips 46 is improved, this configuration also improves accessibility to the tissue and provides the user the ability to straddle the desired vessel for coagulation of the vessel or tissues. It also provides the user the ability to maintain an optimal fixed distance between electrodes 16.

Aspiration lumen 36 serves to aspirate bodily fluid, as well as fluid exiting irrigation lumens 44 at distal tips 46 and/or fluids and materials exiting delivery lumen 38, thereby creating a clear surgical field. Optional fluid lumen 38 may be operatively connected to syringe 24 and permits selective deployment of fluid to a surgical field, such as, for example, saline or other fluid. By providing optional fluid lumen 38, the user is provided with an opportunity to control fluid delivery at certain times during a surgical procedure, for example to selectively flush the surgical field. Optional fluid lumen 38 is disposed on an opposite portion of distal end 34 than aspiration lumen 36 such that connection ends 41 of electrodes are positioned between aspiration lumen 36 and fluid lumen 38. This configuration prevents fluid delivered from fluid lumen 38 from being immediately aspirated into aspiration lumen 36.

Fluid delivery through the irrigation lumen 44, as well as optional fluid lumen 38, provides for coagulation in a controlled wet field. Moreover, the fluid from irrigation lumens 44 also acts as a conductor between electrodes 16 and in the treatment pathway 48, while reducing any heat generated between the electrodes 16 during cauterization to minimize collateral burning of adjacent tissue. Moreover, carbonized buildup at distal tips 46 is minimized, due to the irrigation provided to the electrodes 16.

Figure 2B:
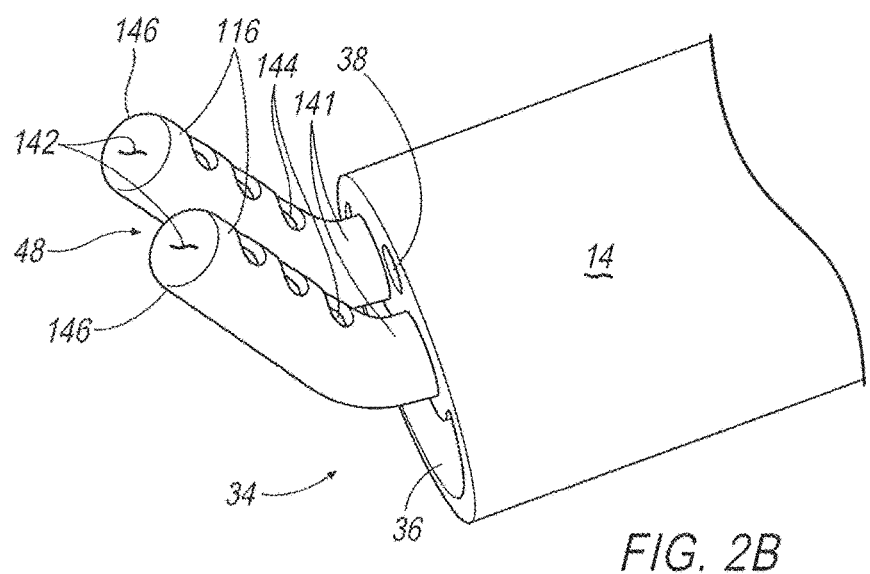
FIG. 2B is an enlarged view of area 2 of FIG. 1 depicting a second exemplary arrangement of a distal end of the bi-polar surgical instrument.

An alternative configuration of distal end 34 of shaft member 14 is illustrated in FIG. 2B. Shaft member 14 in FIG. 2B may be configured the same as that shown in FIG. 2A. Electrodes 116 are similar to that shown in the embodiment of FIG. 2A in that electrodes 116 also include connection ends 141 that are sealed within electrode channels 40 and distal tips 146 are angled away from aspiration lumen 36. However, distal tips 146 are closed with end caps 142. Moreover, one or more irrigation openings 144 are formed within electrodes 116. In one exemplary arrangement, electrodes 116 are provided with a plurality of irrigation openings 144. Irrigation openings 144 are in communication with an inner lumen formed within electrodes 116. Irrigation openings 144 may also be configured with predetermined sized diameters so as to deliver a desired flow rate of fluid through electrodes 116. In one exemplary arrangement, irrigation openings 144 are oriented away from aspiration lumen 38 such that fluid is not immediately aspirated into aspiration lumen 38 upon delivery.

Figure 2C:
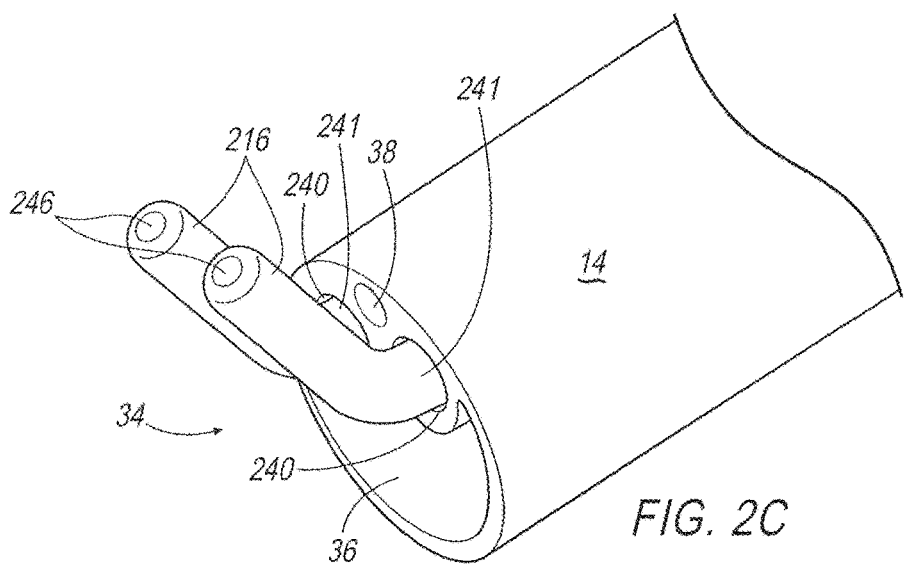
FIG. 2C is an enlarged view of area 2 of FIG. 1 depicting a third exemplary arrangement of a distal end of the bi-polar surgical instrument.

Turning to FIG. 2C, a further alternative arrangement of distal end 34 of shaft member 14 is shown. Shaft member 14 in FIG. 2C may be configured similar to that shown in FIGS. 2A-2B. Electrodes 216 include connection ends 241 that are disposed within electrode channels 240. Electrodes 216 differ from electrodes 16 and 116 in that electrodes 216 are configured as solid members, rather than having an internal lumen. Distal tips 246 of electrodes are angled away from aspiration lumen 36, similar to distal tips 46, 146.

Electrode channels 240 are configured have a diameter that is slightly larger than the diameter of the electrodes 216 such that a gap is formed between an outer surface of electrodes 216 and an inner surface 243 (best seen in FIG. 3B) of electrode channels 240. The gap serves as an irrigation annulus to provide fluid to the surgical field, adjacent electrodes 216. The size of electrode channels 240 are selected to provide a self-regulating and predetermined flow rate. Optional fluid lumen 38 is disposed radially outwardly from electrode channels 240 and opposite aspiration lumen 36.

Figure 2D:
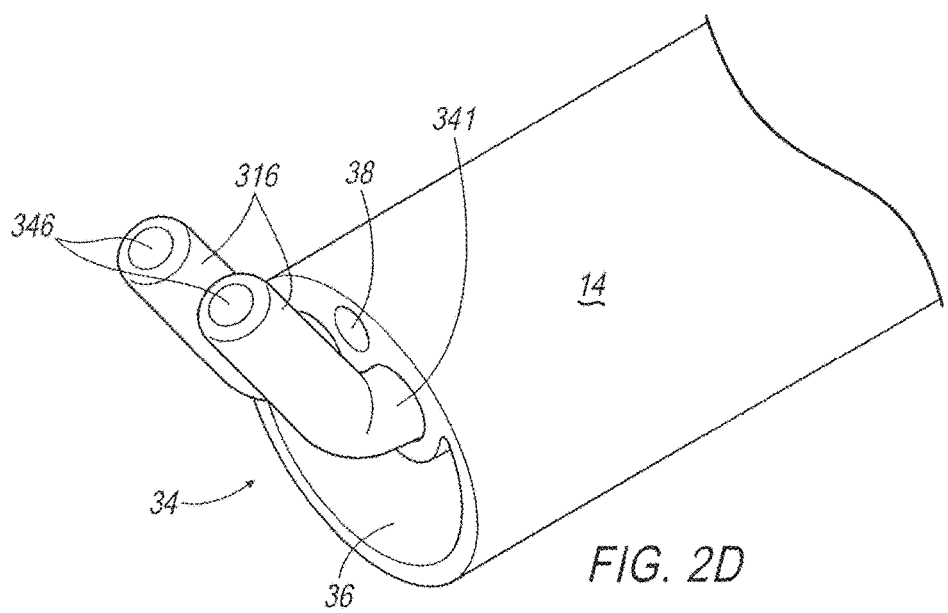
FIG. 2D is an enlarged view of area 2 of FIG. 1 depicting a fourth exemplary arrangement of a distal end of the bi-polar surgical instrument.

Another embodiment of distal end 34 of shaft member 14 is shown is shown in FIG. 2D. Shaft member 14 in FIG. 2D may be configured generally the same as that shown in FIGS. 2A-2C. Electrodes 316 include connection ends 341 that are sealed within electrode channels 40, similar to that shown in FIGS. 2A-2B. Electrodes 316 are also configured similar to that that arrangement shown in FIG. 2C, in that electrodes 316 are configured as solid members, rather than having an internal lumen. Distal tips 346 of electrodes 316 are angled away from aspiration lumen 36, similar to distal tips 46, 146, and 246.

Irrigation is supplied by fluid lumen 38. In the configuration shown in FIG. 2D, fluid lumen 38 is required, if it is desired that surgical instrument 10 provides fluid. In one arrangement, fluid lumen 38 may be selected to have a predetermined diameter so as to be self-regulating at a desired flow rate.

Figure 2E:
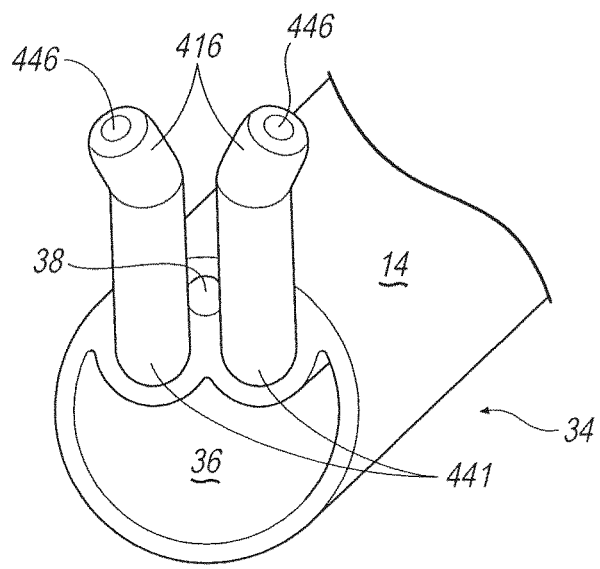
FIG. 2E is an enlarged view of area 2 of FIG. 1 depicting a fifth exemplary arrangement of a distal end of the bi-polar surgical instrument.
Figure 2F:
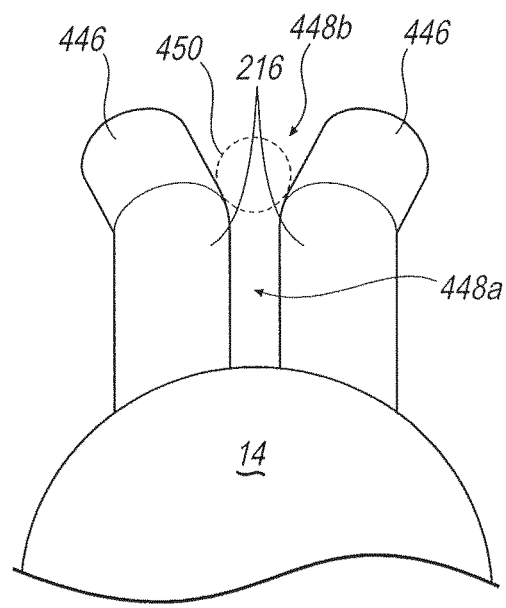
FIG. 2F is an enlarged end view from a proximal direction of the distal end of the bi-polar surgical instrument depicted in FIG. 2E.

A further alternative arrangement of distal end 34 of shaft member 14 is shown in FIGS. 2E-2F. Shaft member 14 in FIG. 2E may be configured to be generally the same as that shown in FIGS. 2A-2D. Electrodes 416 include connection ends 441 that are sealed within electrode channels 40, similar to that shown in FIGS. 2A-2B. Electrodes 416 may also be configured similar to that that arrangement shown in FIG. 2C, in that electrodes 416 may be configured as solid members, rather than having an internal lumen. However, it is understood that electrodes 416 may alternatively be configured with internal lumens, such as that shown in FIGS. 2A-2B and be provided with irrigation lumens positioned in either distal tips 446, similar to FIG. 2A or along the length of electrodes, as shown in FIG. 2B. Distal tips 446 of electrodes are angled away from aspiration lumen 36, similar to distal tips 46, 146, 246, 346. Further, in this exemplary arrangement, distal tips 446 of electrodes 416 are also splayed apart as best seen in FIG. 2F. This configuration defines a treatment passage 448 having a first treatment passage portion 448a formed by a parallel arrangement of electrodes 416. A second treatment passage portion 448b expands outwardly from first treatment passage portion 448a and is defined by electrodes 416 that are angled away from one another. This configuration permits compression of blood vessels 450 (shown in phantom) while cauterization is occurring.

Irrigation is supplied is supplied by fluid lumen 38. In the configuration shown in FIG. 2D, fluid lumen 38 is required, if it is desired that surgical instrument 10 provides fluid. In one arrangement, fluid lumen 38 may be selected to have a predetermined diameter so as to be self-regulating at a desired flow rate or may be controlled from an external regulated source.

Figure 2G:
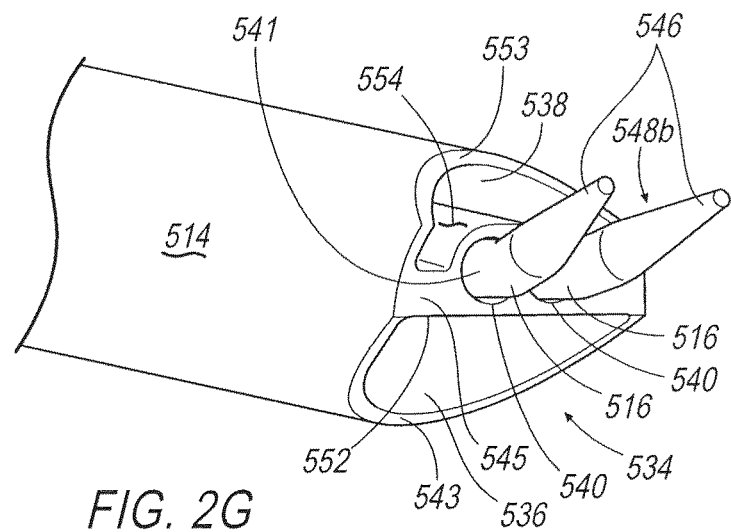
FIG. 2G is an enlarged view of area 2 of FIG. 1 depicting a fifth exemplary arrangement of a distal end of the bi-polar surgical instrument.

A further alternative arrangement of distal end 534 of shaft member 514 is shown in FIG. 2G. Distal end 534 is configured with an aspiration lumen 536, a fluid lumen 538, and electrode channels 540. Electrodes 516 are disposed within electrode channels 540.

Aspiration lumen 536 is positioned below electrode channels 540. Aspiration lumen 536 is defined by a bottom wall portion 543 and a bottom surface 552 of a land area 545. As may be seen in FIG. 2G, bottom wall portion 543 of aspiration lumen 536 may be beveled in a rearward direction. This arrangement prevents aspiration lumen 536 from being occluded during the simultaneous use of the coagulation function of surgical device 10.

Fluid lumen 538 is formed above electrode channels 540. Fluid lumen 538 is defined by a top wall portion 553 and a top surface 554 of land area 545. Top wall portion 553 of fluid lumen 538 may also beveled in a rearward direction. This arrangement increases the field of view for a user, providing better visualization of distal tips 546 of electrodes 516 during use. Fluid lumen 538 permits selective delivery of fluid to the surgical field to facilitate and effectively manage the ability of a user to deliver any additional needed fluid to a surgical site in an in-line orientation, often also described as a coaxial arrangement. Examples of such fluid include, but are not limited to, a saline flush or delivery of a suitable hemostatic agent. However, it is understood that fluid lumen 538 is optional and may be omitted.

Electrode channels 540 are formed within land area 545. In one exemplary arrangement, electrode channels 540 are each sized to have a diameter that is larger than the diameter of a connection end 541 of electrode 516, similar to the construction illustrated in FIG. 2C, so as to form an irrigation annulus. As discussed above, delivery of fluid through electrode channels 540 results in fluid, such as saline, being delivered over the electrodes 516 for precision cooling of the electrodes 516 while it is energized, as well as the tissue. This configuration will reduce "sticktion" whereby tissue being cauterized may "stick" to the electrode, running the risk of creating tearing as the electrodes 516 are moved away from the vessel. In addition, this configuration creates a low energy level that needs to be delivered to the tissue to accomplish coagulation, as opposed to the higher energy level's used for prior art devices. For example, traditional bipolar devices use a 25-35 unit setting on a generator to accomplish the necessary coagulation effect. The current arrangement permits use of a much lower setting on the order of 10 units, for example, thereby significantly improving the dosimetery of the energy and minimizing collateral tissue impact from the energy delivered to the tissue. Moreover, this configuration also reduces (and in some instances virtually eliminates) the traditional peripheral energy spread of the energy field. The use of lower energy means a lower collateral tissue impact. In certain surgical procedures, including, for example, neurological surgery, minimizing collateral impact of the energy is very important to preserve impact to tissue function.

The delivery of fluid to each of the electrode channels (in any of the above embodiments) produces a notable outcome. As mentioned above, the fluid may reduce "sticktion". Further, as the fluid is delivered, the fluid absorbs heat generated by the electrodes, which is an unwanted byproduct generated by the use of RF energy to the electrodes. Due to the configuration of the electrode channels, the temperature of the fluid being delivered is within a desired temperature range that induces and/or facilitates the clotting process. In one exemplary arrangement, the temperature is approximately 120 degrees F. The process described above, i.e., whereby the saline absorbs the heat generated by the electrodes, is different than arrangements whereby saline is energized by electrically charging the saline. Indeed, arrangements where saline is energized by electrically charging the saline is contra-indicated for procedures that are utilized in brain tissue.

As an alternative arrangement, electrodes 516 may be sealed within electrode channels, thereby omitting the irrigation annulus 540, similar to the configurations illustrated in FIGS. 2A-2B and 2D-2E. In such an arrangement, electrodes 516 may be configured with irrigation lumens, similar to that shown in FIG. 2A. Alternatively, irrigation may be supplied through fluid lumen 538. Irrigation provided through such lumens would also be heated by the electrodes, as described above.

Electrodes 516 also include distal tips 546. In the embodiment illustrated in FIG. 2G, distal tips 546 are configured to taper toward the distal end of distal tips 546, so as to form a cone-shaped profile. This configuration provides improved visualization, as well as permits a desired orientation of electrodes 516 while working in a narrow surgical corridor. Moreover, this configuration creates an atraumatic tip, thereby minimizing the ability to unintentionally cut or pierce tissue or a vessel during use.

Electrodes 516 are positioned such that connection ends 541 are arranged to be parallel to one another, thereby creating a treatment pathway similar to treatment pathway 448a. However, similar to the arrangement illustrated in FIGS. 2E-2F, distal tips 546 are splayed so as to oriented away from one another, thereby creating a V-shaped portion 548b to the treatment pathway. This configuration and orientation permits electrodes 516 to straddle a vessel, thereby focusing and delivering the energy of the electrodes 516 to the vessel to be coagulated, but not the surrounding tissues. The bend at connection end 541 of electrodes also permits the electrodes 516 to be placed, when desired, parallel to a vessel to be coagulated, thereby minimizing the damage caused by the electrode 516 "digging into" to an underlying tissue substrate.

Referring to FIGS. 2H-2K, a further embodiment of distal end 634 of shaft member 614 is illustrated. Distal end 634 of shaft member 614 is similar to distal end 534 of shaft member 514 in that distal end 634 is configured with an aspiration lumen 636, a fluid lumen 638, and electrode channels 640 that have a similar configuration as to that shown in FIG. 2G. Electrodes 616 also have a similar configuration as to electrodes 516 and are disposed within electrode channels 640.

For example, aspiration lumen 636 is formed below electrode channels 640. Aspiration lumen 636 is defined by a bottom wall portion 643 and a bottom surface 652 of a land area 645. As may be seen in FIGS. 2H and 2I, bottom wall portion 643 of aspiration lumen 636 may be beveled in a rearward direction. Undercuts 658 are in communication with bottom wall portion 643. Undercuts 658 cooperate with the beveled bottom wall portion 643 to prevent aspiration lumen 636 from being occluded during use.

Figure 2H:
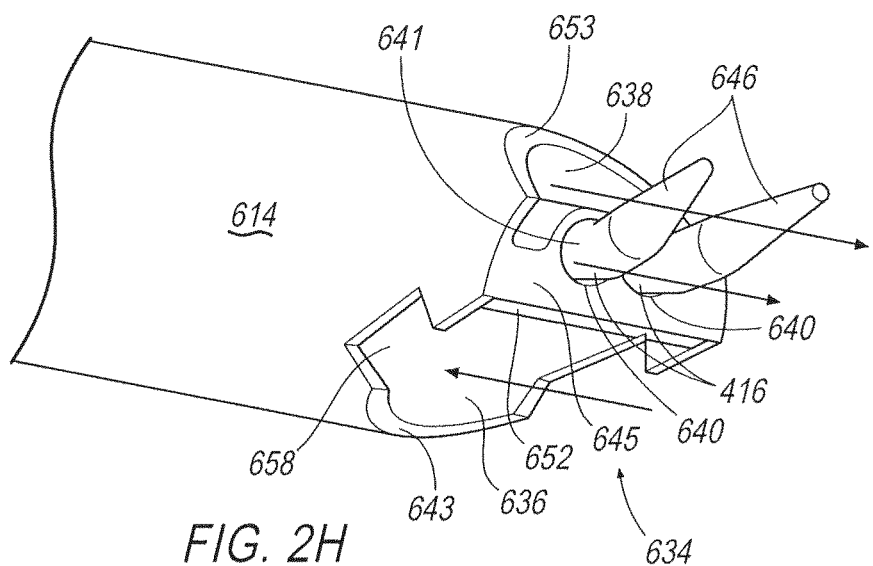
FIG. 2H is an enlarged view of area 2 of FIG. 1 depicting a sixth exemplary arrangement of a distal end of the bi-polar surgical instrument.
Figure 2I:
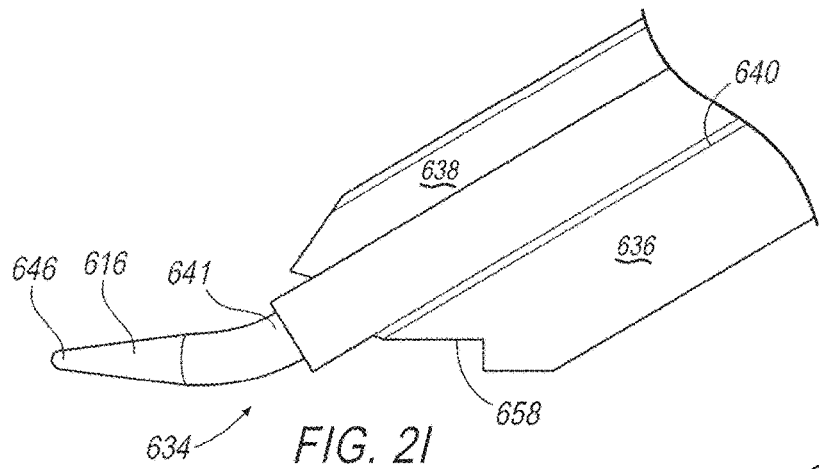
FIG. 2I is an enlarged side cross-sectional view of the exemplary arrangement of the distal end of the bi-polar surgical instrument illustrated in FIG. 2H.
Figure 2J:
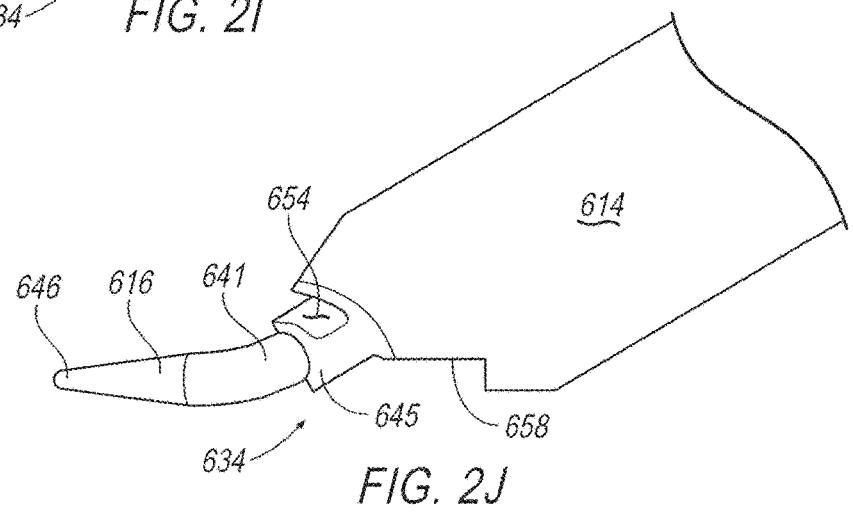
FIG. 2J is an enlarged side view of the exemplary arrangement of the distal end of the bi-polar surgical instrument illustrated in FIG. 2H.
Figure 2K:
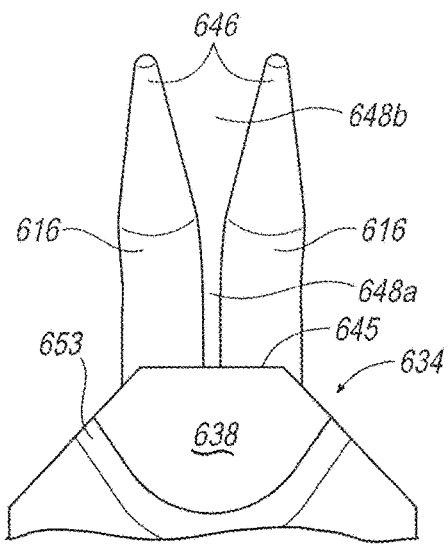
FIG. 2K is a top view of the exemplary arrangement of the distal end of the bi-polar surgical instrument illustrated in FIG. 2H.
Figure 2L:
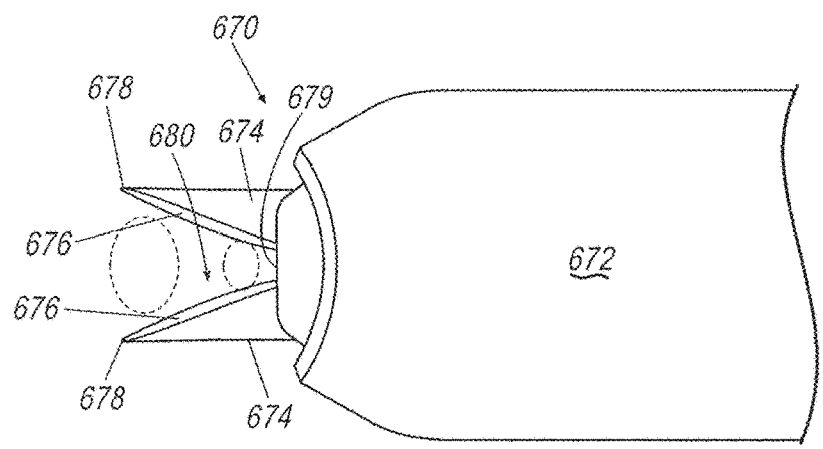
FIG. 2L is a top view of an exemplary arrangement of the distal end of a bi-polar surgical instrument.
Figure 2M:
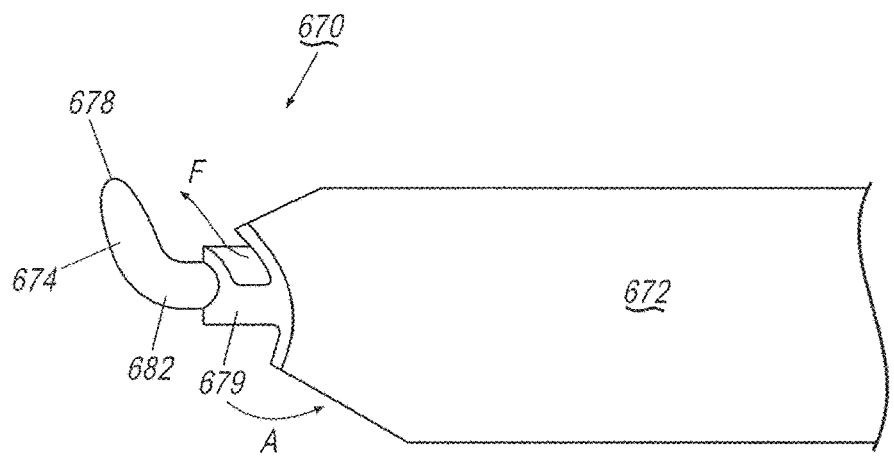
FIG. 2M is a side elevational view of the arrangement shown in FIG. 2L.
Figure 2N:
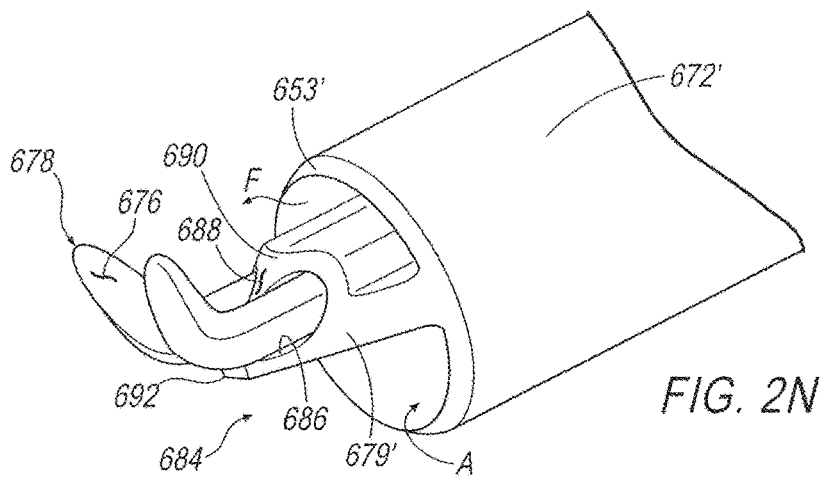
FIG. 2N is a perspective view of the arrangement shown in FIGS. 2K and 2L, slightly modified.

Turning to FIGS. 2L-2M, a further alternative arrangement of a distal end 670 of a shaft member 672 is shown. Shaft member 672 in FIG. 2M may be configured generally the same as that shown in FIGS. 2H-2J, in that distal end 670 is configured with an aspiration lumen similar to that shown in FIG. 2I, a fluid lumen that is configured generally the same as that shown in FIG. 2I, and electrode channels that have a similar configuration as to that shown in FIG. 2H. Electrodes 674 are disposed within the electrode channels in a similar manner as shown in FIG. 2H.

However, in the arrangement shown in FIGS. 2L-2M, electrodes 674 are configured with generally opposing engagement surfaces 676 that cooperate to define a treatment pathway 680. Engagement surfaces 676 may be constructed to be generally planar. In one exemplary configuration, best seen in FIG. 2L, engagement surfaces 676 are oriented such that engagement surfaces 676 at tip members 678 are displaced further away from one another than engagement surfaces 676 adjacent a land area 678 of shaft member 672 such that a generally V-shaped treatment pathway 680 is created. This configuration allows for electrodes 674 to straddle a vessel, thereby focusing and delivering the energy of the electrodes 516 to the vessel to be coagulated, but not the surrounding tissues. Moreover, the V-shape treatment pathway 680 also serves to accommodate different sized vessels, represented in phantom in FIG. 2L. In one exemplary configuration, the distance between engagement surfaces 676 at tip member 678 is approximately 0.07 inches, while the distance between engagement surfaces 676 adjacent land member 678 is approximately 0.01.

As illustrated in FIG. 2M, electrodes 674 are configured as bent at 682. This configuration permits the electrodes 674 to be placed, when desired, parallel to a vessel to be coagulated, thereby minimizing the opportunity for damage to be caused by the electrodes 674 "digging into" to an underlying tissue substrate.

As discussed above, an aspiration lumen may be formed below electrode channels into which electrodes 674 are positioned. Aspiration, indicated by arrow A is directed into the aspiration lumen under electrodes 674. The aspiration lumen may be configured as shown in FIG. 2G or 2H and a bottom wall portion that defines the aspiration lumen may be beveled. While not shown, undercuts may also be provided.

A fluid lumen, similar to that which is shown in FIG. 2H may also be provided. A top wall portion that defines the fluid lumen may be beveled. This arrangement increases the field of view for a user, providing better visualization of distal tips 678 of electrodes 674 during use. The fluid lumen permits selective delivery of fluid represented by arrow F (as shown in FIG. 2M) to the surgical field to facilitate and effectively manage the ability of a user to deliver any additional needed fluid to a surgical site in an in-line orientation. The ability to simultaneously provide irrigation, aspiration an coagulation in a common plane as a co-axial configuration whereby the irrigation channel is above the electrodes and the aspiration channel is below the electrodes allows the user to irrigate the surgical field sufficiently with a "flushing action" of the irrigant exiting the irrigation channel in the same plane as the electrodes while the surgeon accurately controls the quantity of fluid aspirated from the surgical field so as to provide a clear field of view of where the actual bleeding vessel is originating from. This provides the surgeon the ability to accurately and precisely deliver coagulation to the offending vessel without damage to collateral tissues due to blindly digging, probing and burning the collateral tissues in search of the offending vessel.

Referring to FIG. 2N, a further exemplary arrangement of a distal end 684 of handpiece 672 is illustrated. The arrangement in FIG. 2N is generally the same as that of FIGS. 2L and 2M, except that the land area 679' has been slightly modified. Accordingly, identical elements have been given identical reference numbers as the arrangement shown in FIGS. 2L-2M.

The land area 679' is positioned between a fluid lumen where fluid F is configured to exit from the distal end 684 of the handpiece 672' and an aspiration lumen that is configured to aspirate A fluid from a surgical site. Formed within the land area 679' are electrode channels 686 through which electrodes 678 protrude. Electrode channels 686 are sized to be larger than a diameter of the electrodes 678 such that electrode channels 686 may be used to deliver fluid therethrough as discussed above in connection with previous alternative arrangements, such as, for example, FIG. 2G-2H. The land area 679' further differs from land area 679 in that is extends further away from the distal end 684 of the handpiece 672', thereby enhancing visibility. In addition, a front face 688 may be angled so as to slope distally outward from a top edge 690 to a bottom edge 692. As may be seen in FIG. 2N, bottom edge 692 is positioned distally of the top edge 690.

Handpiece 672' may be configured similar to handpiece 672. Alternatively, top wall portion 653' and bottom wall portion 642' may only include a slight bevel around the circumference of distal end 684 of handpiece 672'.

Figure 3A:
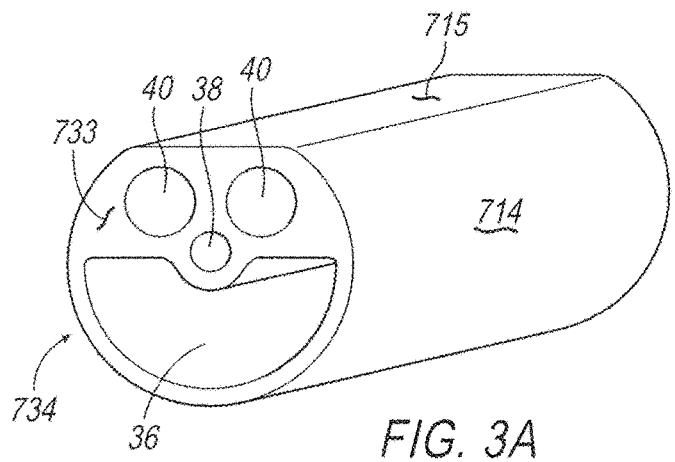
FIG. 3A is an exemplary arrangement of a shaft member of the bi-polar surgical instrument of FIG. 1.
Figure 3B:
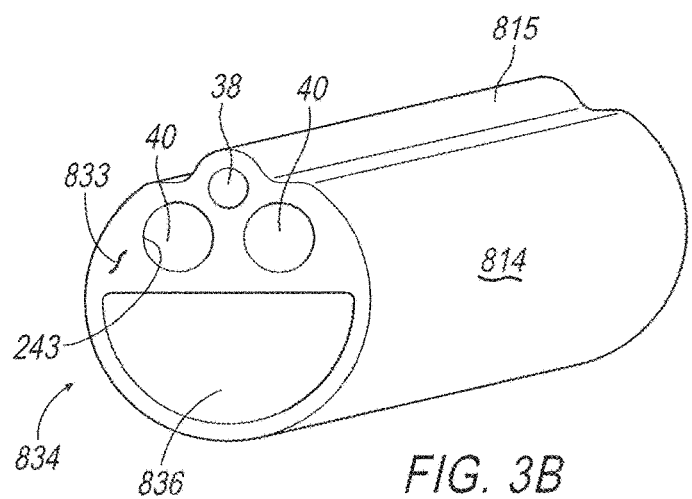
FIG. 3B is an alternative exemplary arrangement of a shaft member of the bi-polar instrument of FIG. 1.

Referring to FIGS. 3A-3B, exemplary alternative options for a distal end of a shaft member are illustrated. More specifically, as illustrated in FIG. 3A, distal end 734 of a shaft member 714 is illustrated. Distal end 734 may be configured with a generally planar end face 733. Electrode openings 40 and aspiration lumen 36 extend proximally from end face 733. Fluid lumen 38 also extends proximally from end face 733. In the arrangement illustrated in FIG. 3A, fluid lumen 38 is positioned above aspiration lumen 36, but below and between electrode openings 40. Aspiration lumen 36 is contoured around fluid lumen 38. To reduce the profile of shaft member 714 and improve visibility of electrodes (not shown), a portion of shaft member 714 positioned above electrode openings 40 may be beveled to create a generally planar surface 715.

FIG. 3B illustrates another alternative arrangement of a distal end 834 of a shaft member 814. In this arrangement, distal end 834 may be configured with a generally planar end face 833. Electrode openings 40 and aspiration lumen 36 extend proximally from end face 733. Fluid lumen 38 also extends proximally from end face 733 and is positioned above, and between electrode openings 40, similar to the configuration shown in FIGS. 2A-2E. To reduce the profile of the shaft member 814 and improve visibility of distal end 834, top surface 815 of shaft member 814 is contoured around fluid lumen 38.

Figure 4A:
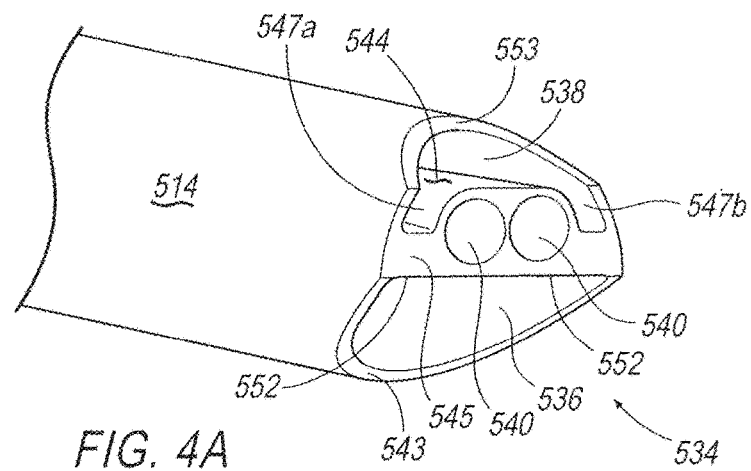
FIG. 4A is a third alternative exemplary arrangement of a shaft member of the bi-polar instrument of FIG. 1.

FIG. 4A illustrates the arrangement of distal end 534 of shaft member 514, with electrodes 516 removed. As may be seen, fluid lumen 538 is separated from aspiration lumen 536 by a land area 545. Land area 545 is contoured around electrode channels 540 to form side channels 547a, 547b. Side channels 547a, 547b permits fluid to be directed above and alongside electrodes 516.

Figure 4B:
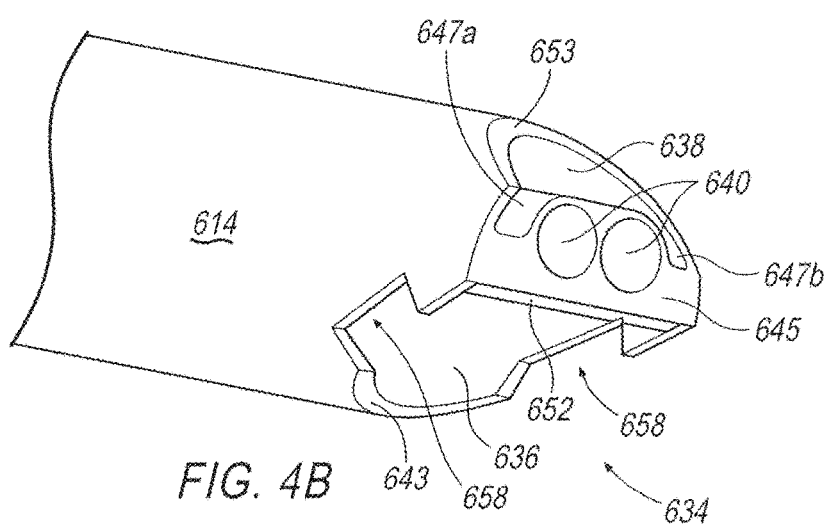
FIG. 4B is a fourth alternative exemplary arrangement of a shaft member of the bi-polar instrument of FIG. 1.

FIG. 4B illustrates the arrangement of distal end 634 of shaft member 614, with electrodes 616 removed. Fluid lumen 638 is separated from aspiration lumen 636 by a land area 645, similar to that shown in FIG. 4A. Land area 645 is also contoured around electrode channels 640 to form side channels 647a, 647b. Side channels 647a, 647b permits fluid to be directed above and alongside electrodes 616.

Figure 5:
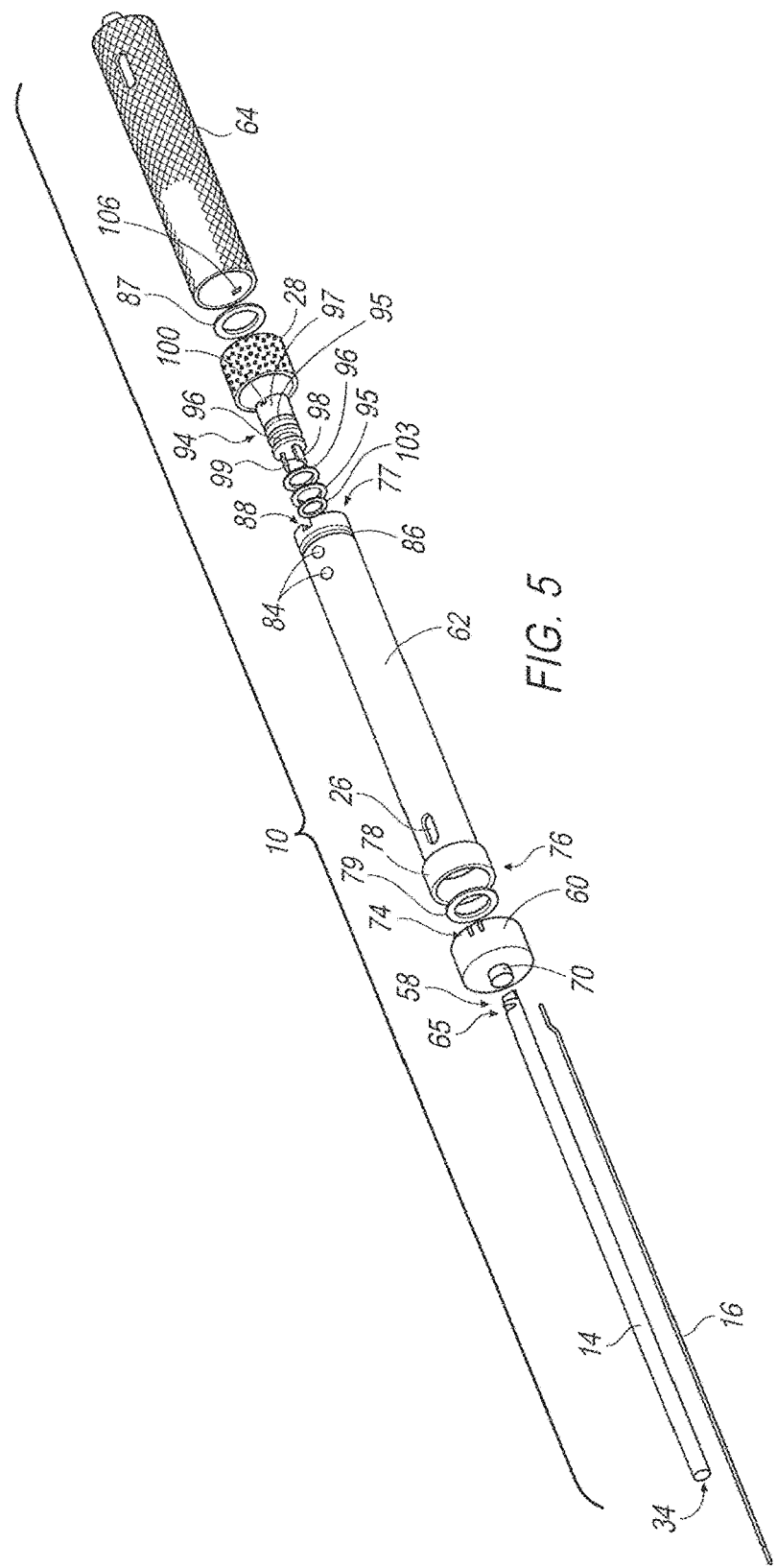
FIG. 5 is a partially exploded view of the bi-polar instrument.
Figure 6:
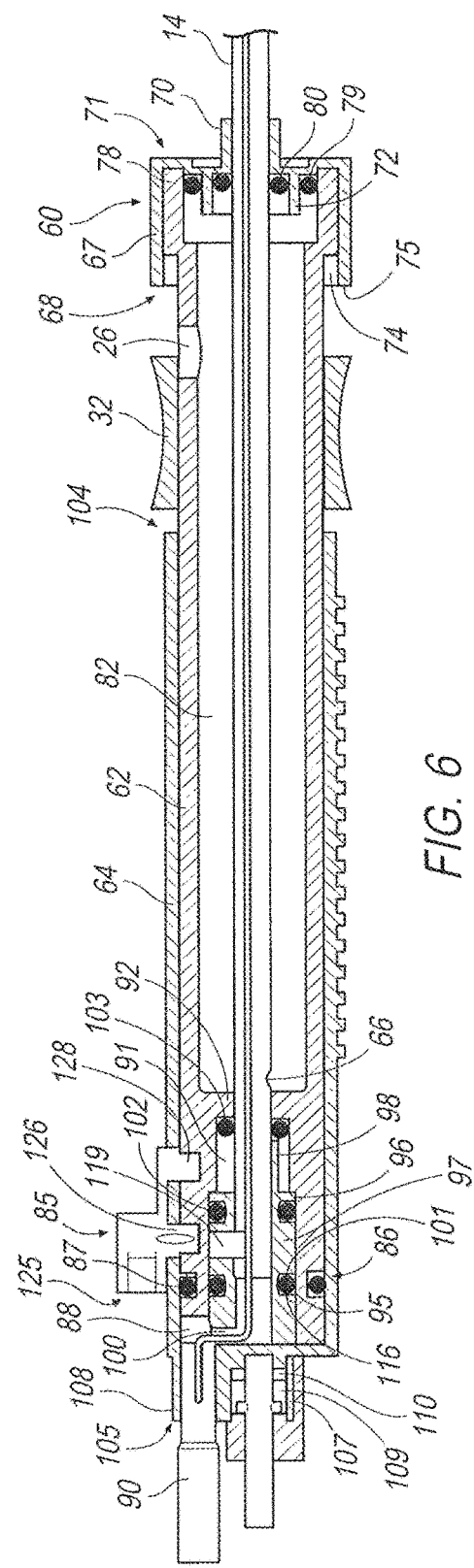
FIG. 6 is a cross-sectional view of the bi-polar instrument of FIG. 5.
Figure 7A:
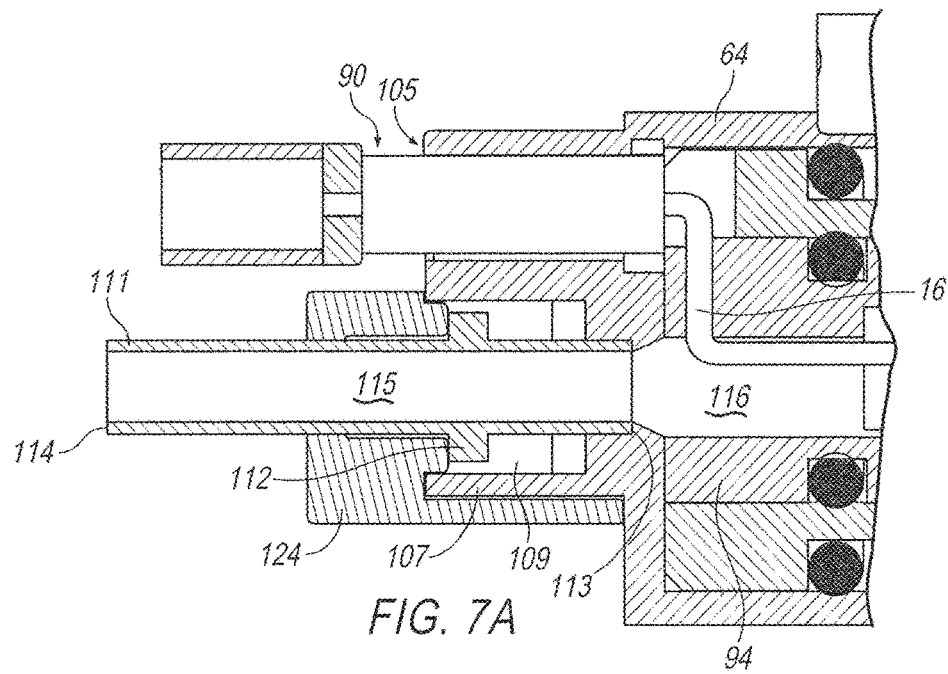
FIG. 7A is an enlarged view of area 7A from FIG. 6 depicting a proximal end of the bi-polar instrument of FIG. 5.
Figure 7B:
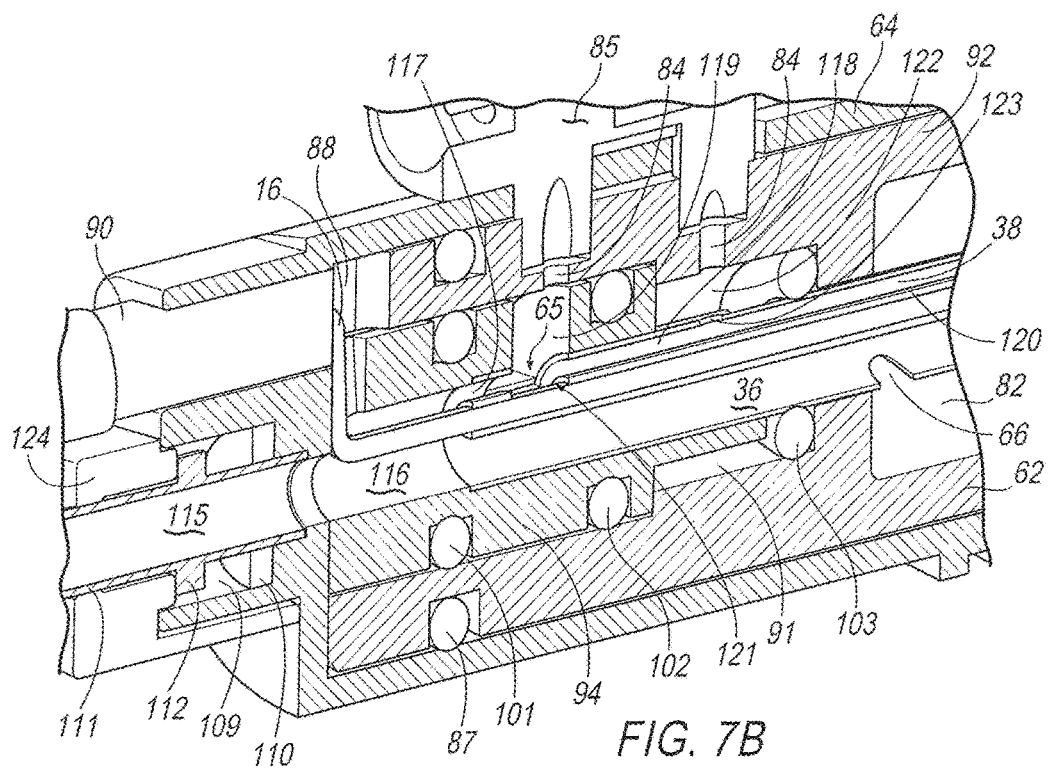
FIG. 7B is an enlarged cross-sectional perspective view of the proximal end of the bi-polar instrument of FIG. 5.

FIG. 5 illustrates an exploded view of surgical instrument 10. FIGS. 6-7B illustrate cross-sectional views of surgical instrument 10. Turning to FIG. 5, surgical instrument 10 comprises shaft member 14, a cap member 60, an inner sleeve 62, an outer sleeve 64, control valve 28, and electrodes 16 (only one of which is depicted in FIG. 5). Shaft member 14 is defined by distal end 34 and a proximal end 58. An irrigation opening 65 is formed through a portion of shaft member 14, as will be explained in further detail below. Irrigation opening 65 is configured to cooperate with a fluid supply. A vacuum relief opening 66 (best seen in FIG. 7B) is also formed through a portion of shaft member 14. Vacuum relief opening 66 is configured to communicate with a vacuum chamber 82, as will be discussed below.

Cap member 60, best seen in FIG. 6, is defined by a body member 67 having an open proximal end 68 and shaft reinforcement member 70 that extends from a distal end face 71 of cap member 60. An inner seal mount 72 extends inwardly from distal end face 71. Receiving grooves 74 (best seen in FIG. 8) are formed on a proximal edge 75 of proximal end 68. Receiving grooves 74 are configured to frictionally retain slidable sleeve 32 of control valve 28, as will be explained below in further detail.

Inner sleeve 62 is defined by a distal end 76 and a proximal end 77. A sealing collar 78 is fixedly connected to inner sleeve 62 at distal end 76. As best seen in FIG. 6, sealing collar 78 cooperates with inner seal mount 72 of cap member 60 to secure sealing members 79 and 80 (only one of which is shown in FIG. 5). Sealing member 79 is disposed between sealing collar 78 and inner seal mount 72. Sealing member 80 is disposed between inner seal mount 72 and shaft member 14.

Inner sleeve 62 further includes vent opening 26. As will be explained in further detail below, vent opening 26 cooperates with slidable sleeve 32 to selectively cover and uncover vent opening 26 to vary the level aspiration being delivered through aspiration lumen 36. As best seen in FIG. 6, vent opening 26 is in communication with a vacuum chamber 82 that is in communication with a vacuum relief opening 66 (best seen in FIG. 7B) that is formed in shaft member 14.

Proximal end 77 of inner sleeve 62 includes openings 84 for introduction of fluid into surgical device 10. More specifically, a fluid connector 85 (best seen in FIGS. 6 and 7B) is configured to cooperate with openings 84 to deliver fluid through shaft member 14.

A sealing groove 86 is formed in the outer surface of outer sleeve 62. Sealing groove 86 is configured to receive a sealing member 87. Sealing member 87 serves to provide a seal between outer sleeve 62 and outer sleeve 64. An electrode opening 88 is formed through proximal end 77 inner sleeve. Electrode opening 88 permits a connection end of electrodes 16 to be joined to a connection port 90, as seen in FIGS. 6-7B. A proximal chamber 91 is formed within proximal end 77 of inner sleeve 62. A radially inward extending rib 92 separates proximal chamber 91 and vacuum chamber 82.

Surgical instrument 10 further comprises an inner mounting member 94 that is positioned in proximal chamber 91 of inner sleeve 62 (as may be seen in FIG. 6). Inner mounting member 94 includes a body member 97 having first and second sealing grooves 95, 96 and a distal sleeve 98 having a slit 99 therein. An electrode opening 100 is formed in a proximal end of inner mounting member 94. Electrode opening 100 aligns with electrode opening 88 to provide a pathway for electrodes 16. Sealing members 101 and 102 are received within sealing grooves 96 and 95, respectively, and provides a seal between inner mounting member 94 and inner sleeve 62 so as to provide a sealed fluid pathway for irrigation lumens disposed around or through electrodes 216, including irrigation lumens 44, 144, 240, 540, and 640. An additional sealing member 103 is positioned between a rib 92 and a distal end of inner mounting member 94. Sealing member 103 cooperates with sealing member 102 to provides a fluid pathway that is in communication with fluid lumen 38.

Outer sleeve 64 is defined by a distal end 104 and a proximal end 105. Outer sleeve 64 may include a texturized surface so as to create a gripping surface. An inner portion of outer sleeve 64 may be provided with a receiving groove 106 that engages a detent (not shown) on inner sleeve 62 to secure outer sleeve 64 to inner sleeve 62. Proximal end 105 of outer sleeve 64 includes an aspiration mount 107 and an electrode connection mount 108.

Aspiration mount 107 defines a chamber 109 therein. A flexible washer 110 is seated therein. Aspiration mount 107 is configured to receive an aspiration connection mount 111. Aspiration connection mount 111 includes a flange member 112 that is positioned between distal and proximal ends 113, 114 thereof. An aspiration channel 115 extends therethrough. Distal end 114 of aspiration connection mount 111 is extends through chamber 109 and is configured to selectively rotate within aspiration mount 107. A cap member 124 closes chamber 109. This rotation serves to prevent surgeon fatigue during use. More specifically, weight of an aspiration line operatively connected to the aspiration connection mount 111 will cause the aspiration connection mount 111 to rotate so as to move the aspiration line automatically out of the surgeon's way during a procedure, as opposed to the surgeon needing to rotate his or her operating hand in awkward positions to move the aspiration line. Vacuum grease (not shown) may be positioned between flange member 112 and flexible washer 110 within chamber 109 to assist in rotation. When mounted within aspiration mount 107, aspiration channel 115 is in communication with an aspiration pathway 116 formed in inner mounting member 64.

Aspiration pathway 116 receives shaft member 14 such that aspiration delivered from an aspiration source through aspiration mount 107 is communicated to aspiration lumen 36 of shaft member 14. To isolate fluid delivery from aspiration, areas 117 and 118 are filled with adhesive (not shown) on either side of a fluid channel 119 that is in communication with one of openings 84. Electrode lumens 120 (one of which is visible in FIG. 7B) are mounted within shaft member 14 and define electrode channels 40, which house electrodes 16. In the embodiments where fluid is delivered is delivered through electrode channels 40 (e.g., FIGS. 2C, 2G-2I), electrode lumens 120 are each provided with an irrigation opening 121 that provides communication from irrigation opening 65 to electrode channels 40 to permit irrigation to be delivered around electrodes 16.

A second irrigation chamber 122 is provided between an outer distal surface of inner mounting member 94 and sealing member 103. Irrigation chamber 122 is in communication with one of openings 84 through inner sleeve 62, as well as an opening 123 that is formed within shaft member 14, between irrigation opening 65 and aspiration opening 66. Opening 123 is in communication with fluid lumen 38 and may be sized to provide a controlled flow rate of fluid through the fluid lumen 38.

Connection port 90 is received within electrode connection mount 108. Connection port 90 is configured to receive an electrical source for energizing electrodes 16. A proximal end of electrodes 16 is received within connection port 90 to facilitate delivery of energy.

Fluid connector 85, as best seen in FIG. 6, includes a connection end 125, irrigation tube 126 and fluid tube 128. Irrigation tube 126 is configured to be received within one openings 84, with fluid tube 128 being configured to be received within the other opening 84. Connection end 125 is configured to receive irrigation line 20 and tubing that connects to syringe 24. Fluid from irrigation line 20 is delivered through irrigation lumen 40, while fluid from syringe 24 is delivered through fluid lumen 38.

Figure 8:
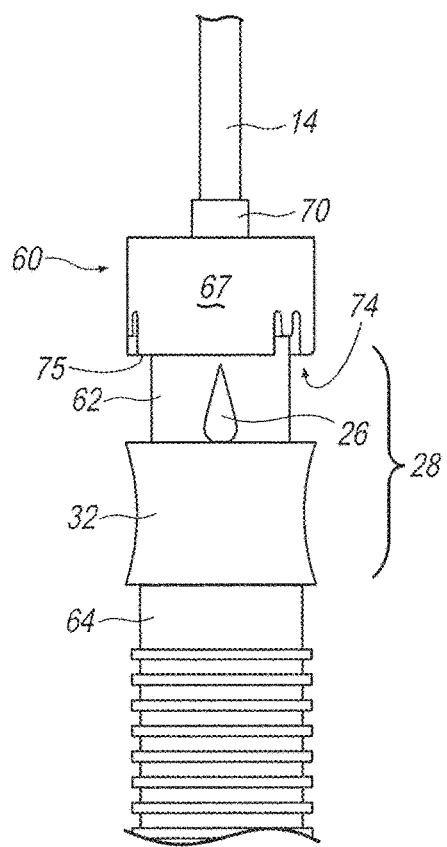
FIG. 8 is an enlarged view of area 8 from FIG. 1 depicting a vent feature of the bi-polar instrument of FIG. 1.

Referring to FIG. 8, control valve 28 is illustrated and will be explained. Control valve 28 comprises vent opening 26 and slidable sleeve 32. Vent opening 26 is in communication with vacuum chamber 82. In on exemplary configuration, vent opening 26 is configured with a teardrop shape, allowing the greatest amount of vacuum to be delivered when the entirety of the vent opening 26 is covered. However, slidable sleeve 32 is configured to be selectively moved to cover or uncover vent opening 26 to immediately vary aspiration being delivered through aspiration lumen 36. More specifically, in the configuration shown in FIG. 8, when it is desired to have full aspiration, slidable sleeve 32 is moved distally to completely cover vent opening 26. A degree of vacuum will immediately be delivered as sleeve 32 advances over the widest portion of the teardrop shape (i.e., the bottom portion). As the slidable sleeve 32 approaches the tip of the teardrop (i.e., the top portion), fine application of vacuum may be applied.

As described above, slidable sleeve 32 may be provided with inner rib members (not shown) that are configured to frictionally engage receiving grooves 74 to retain slidable sleeve 32 to collar 67. When it is desired to reduce aspiration pressure, slidable sleeve 32 is moved in a proximal direction to at least partially expose vent opening 26, thereby venting vacuum chamber 82. When slidable sleeve 32 is moved so as to completely expose vent opening 26, there is no aspiration being delivered to aspiration lumen 36. This configuration is advantageous in that it permits a user to immediately release tissue while in use, as well as reduce aspiration as needed. Due to its position on handpiece 12, slidable sleeve 32 is easy to manipulate with a single hand from any orientation of the user gripping the device, also providing improved ease of use.

In one exemplary arrangement, vent opening 26 has a teardrop shape. This shape permits a controlled reduction of aspiration as slidable sleeve 32 moves proximally. However, it is understood that other shapes of vent opening 26 may be employed. It is also contemplated that other arrangements for operation of the slidable sleeve and vent opening may be utilized. Further examples will be discussed below.

An alternative arrangement of surgical device 200 is shown in FIGS. 9-12. FIG. 9A illustrates an exploded view of surgical device 200. FIG. 10A illustrates a cross-sectional view of surgical device 200. While the distal tip of surgical device 200 is similar to the arrangement shown in FIG. 2G, it is understood that any of the distal tip arrangements illustrated in FIGS. 2A-2N may be employed, including, but not limited to spacing of the electrodes, or the particular configurations of the electrode tips.

Surgical device 200 comprises a shaft member 214, a cap member 260, a sleeve 262, a control valve 228, electrodes 216. An optional stiffening member 215 may also be included. Shaft member 214 is defined by distal end 234 and a proximal end 258. An optional outer sleeve 264 may also be included. An irrigation opening 265 is formed through a portion of shaft member 214, as will be explained in further detail below. Irrigation opening 265 is configured to cooperate with a fluid supply. A flush opening 266 is also formed through a portion of shaft member 214, which also is configured to communicate with a fluid supply. A vacuum relief opening 269 (best seen in FIG. 10B) is also formed through a portion of shaft member 214. Vacuum relief opening 269 is configured to communicate with a vacuum chamber 282 (shown in FIGS. 10A-10B), similar to the arrangement shown in FIG. 6.

Figure 10A:
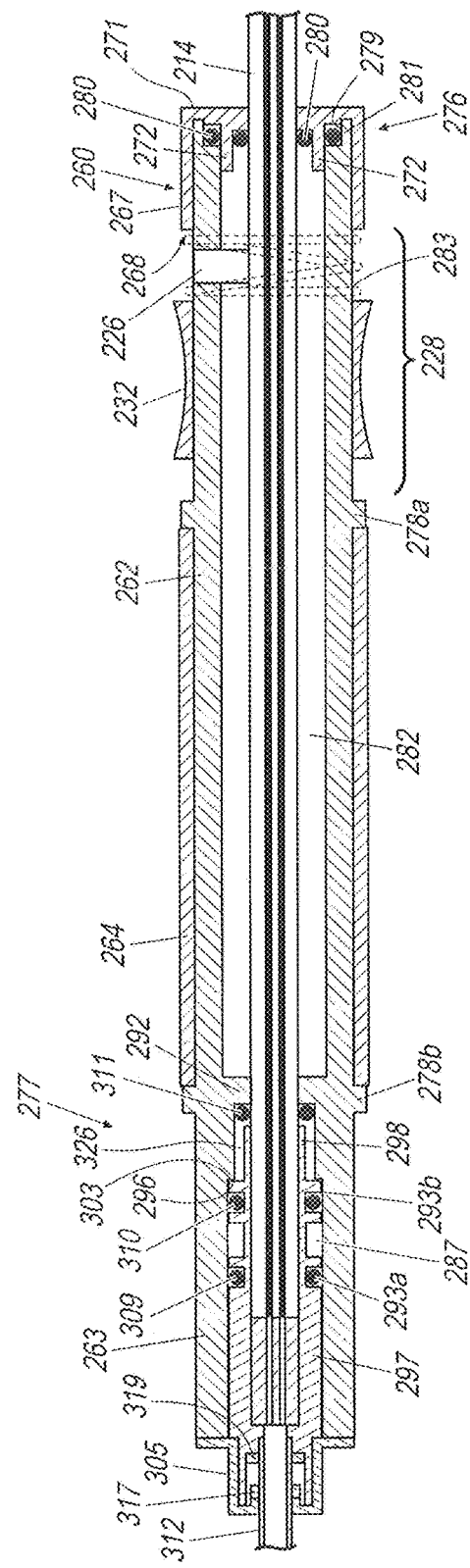
FIG. 10A is cross-sectional top view of the bipolar instrument of FIG. 9A.

Cap member 260, best seen in FIG. 10A, is defined by a body member 267 having an open proximal end 268 and a distal end face 271. An inner seal mount 272 extends inwardly from distal end face 271.

Sleeve 262 is defined by a distal end 276 and a proximal end 277. In one exemplary configuration, first and second support collars 278a, 278b may be fixedly connected to sleeve 262. As best seen in FIG. 10A, support collars 278a, 278b cooperate with outer sleeve 264, which is mounted therebetween. Alternatively, first and second support collars 278a, 278b may be omitted and outer sleeve 264 may be over-molded onto sleeve 262. Outer sleeve 264 may be ergonomic in nature and include gripping elements on an outer surface thereof. In one exemplary arrangement, distal end 276 of sleeve 262 may further comprises a sealing groove 279. Sealing groove 279 cooperates with inner seal mount 272 and distal end face 271 to define a sealing chamber that receives a sealing member 280. In an alternative arrangement, no sealing groove is provided and the sealing member 280 bears against a distal wall face 281 with cap member 260 assembled thereto.

Sleeve 262 further includes vent opening 226. As will be explained in further detail below, vent opening 226 cooperates with a slidable sleeve 232 to define control valve 228.

Figure 10B:
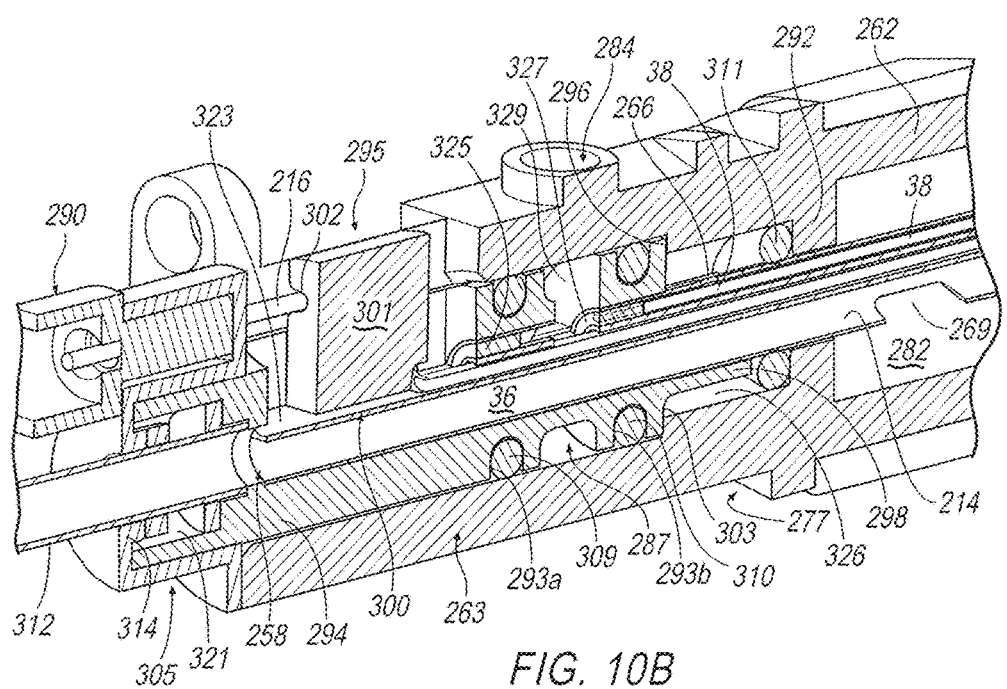
FIG. 10B is an enlarged cross-sectional perspective view of the proximal end of the bipolar instrument of FIG. 9A.
Figure 11:
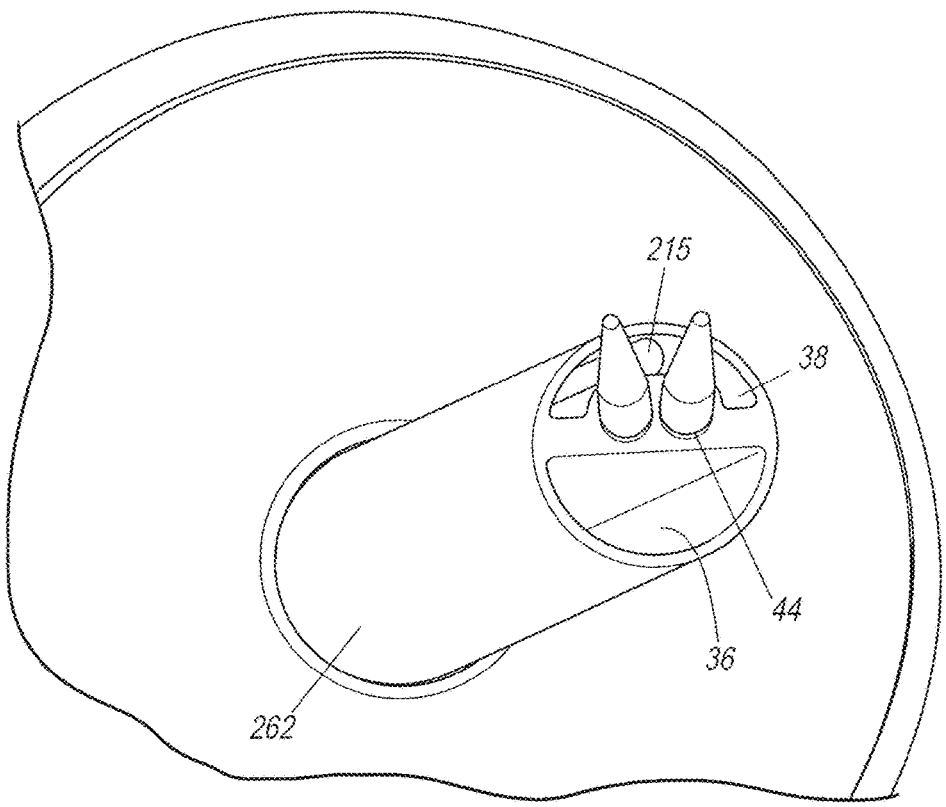
FIG. 11 is a perspective view of a distal end of the bipolar instrument of FIG. 9A.

Slidable sleeve 232 is configured to selectively cover and uncover vent opening 226 to vary the level aspiration being delivered through an aspiration lumen 36 (seen in FIGS. 9B and 11, for example). Further, sleeve 262 is configured to allow a user to grip the surgical device at any ergonomically comfortable position and orientation based upon the needs of the surgical procedure, while still allowing the surgeon to maintain control of the aspiration infinitely and precisely. Vent opening 226 is in communication with vacuum chamber 282 that is in communication with vacuum relief opening 269 (best seen in FIG. 10B) that is formed in shaft member 214. In one exemplary configuration, vent opening 226 has a tear drop shape (see FIG. 9A), to allow for more effective control of venting.

In one exemplary arrangement, the tear drop shape of vent opening 226 is oriented with the widest part of the vent opening 226 toward the proximal end 277 of sleeve 262. In this arrangement, the slidable sleeve 232 may be biased toward the proximal end 277 with a spring member 283, shown in phantom in FIG. 10A. With this configuration, the slidable sleeve 232 is biased toward the proximal end 277 such that the surgical device 200 operation is biased toward no vacuum delivery. However, other exemplary configurations of the interaction of the slidable sleeve and vent opening are contemplated, and will be discussed in further detail below.

In one exemplary configuration, proximal end 277 of sleeve 262 includes an integrally formed hub member 263, allowing for ease of manufacture. However, it is understood that hub member 263 and sleeve 262 may be formed as separate elements without departing from the disclosure. Hub member 263 is generally hollow and includes fluid openings 284 for introduction of fluid into surgical device 200. In one exemplary arrangement, fluid openings 284 may be formed through a mounting plate 285 carried by hub member 263. A fluid connector (not shown) is configured to engage mounting plate 285 and cooperate with openings 284 to deliver fluid through shaft member 214.

In another exemplary arrangement (best seen in FIG. 13), mounting plate 285 is eliminated from hub 263'. Ports 288 that are connected to fluid openings 284 are formed through the hub 263' to which fluid tubes 291a and 291b may be connected. In one exemplary arrangement, the fluid tubes 291a and 291b may be glued directly to the ports 288. In another exemplary arrangement, the ports 288 may be configured with upwardly extending hose barbs (not shown) to which fluid tubes 291a and 291b may be disposed over.

Figure 12:
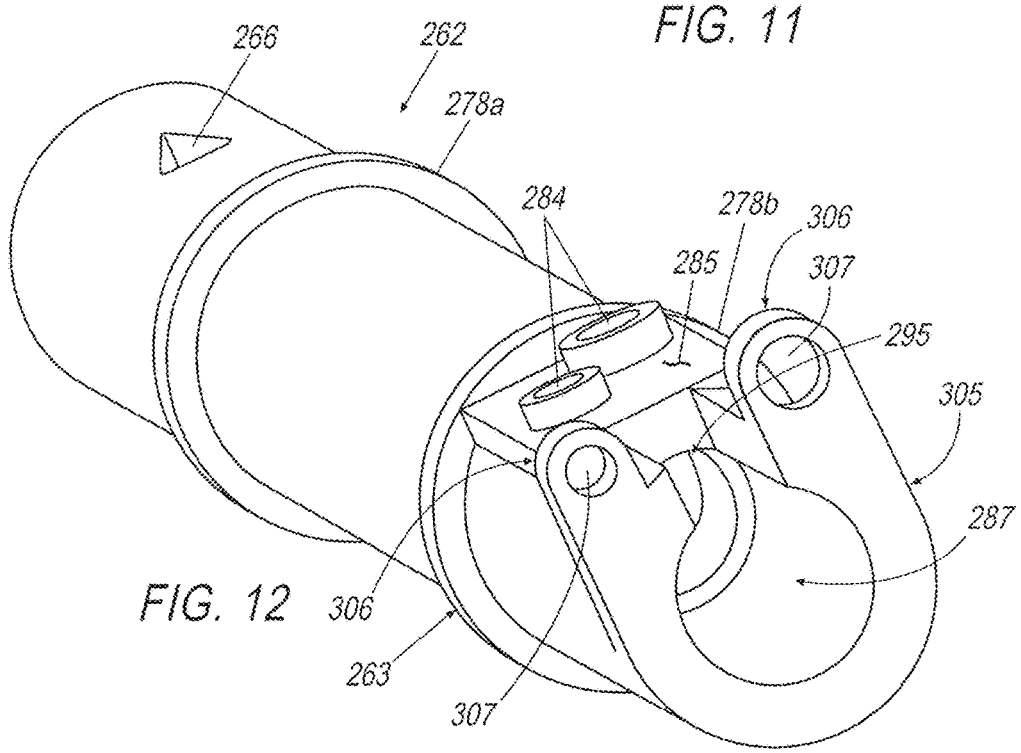
FIG. 12 is a perspective view of a proximal end of a sleeve of the bipolar instrument of FIG. 9A.

In one exemplary arrangement, hub member 263 defines a chamber 287 (see, FIG. 12) therein that is configured to receive an inner mounting member 294 (see FIG. 9A). Inner mounting member 294 will be discussed in greater detail below. As seen in FIGS. 10A-B, Chamber 287 may be configured with a step 296 that engages with a radially extending edge 303 of inner mounting member 294. Hub member 263 may further define a lateral opening 295 (FIG. 12). In one exemplary configuration, an end flange 305 may be disposed on proximal end 277. In one exemplary configuration, end flange 305 includes extension members 306 disposed on either side of lateral opening 295. Extension members 306 may each include openings 307. The openings 307 are configured to receive suitable fluid tubing (such as that shown in FIG. 13) that mates with fluid openings 284.

Inner mounting member 294 is configured to be positioned in chamber 287 of hub member 263. Inner mounting member 294 includes a body member 297 which defines first and second sealing grooves 293a, 293b and a distal sleeve segment 298. An electrode opening 300 is formed through an outer surface of inner mounting member 294. Electrode opening 300 aligns with lateral opening 295 to provide a pathway for electrodes 216. In one exemplary arrangement, a stabilizing member 301 is configured to be received within electrode opening 300. In another exemplary arrangement, stabilizing member is integrally formed with the inner mounting member 294. Stabilizing member 301 includes mounting channels 302 that are configured to secure electrodes 216 within shaft member 214 and direct ends of electrodes 216 to a connection mount 290 formed on an end cap 305. Connection mount 290 is configured to receive a connection port (as shown, for example, in FIG. 13) to operatively connect electrodes 216 to an electrical source for energizing electrodes 216. A proximal end of electrodes 216 will be received within the connection port to facilitate delivery of energy.

Sealing members 309 and 310 are received within sealing grooves 293*a* and 293*b*, respectively, and provides a seal between inner mounting member 294 and sleeve 262 so as to provide a sealed fluid pathway for irrigation lumens disposed around or through electrodes 216, including irrigation lumens 44, 144, 240, 540, and 640. (see, e.g., FIG. 11). An additional sealing member 311 is positioned between a rib 292 and a distal end of inner mounting member 294. Sealing member 311 cooperates with sealing member 293*b* to provide a fluid pathway that is in communication with fluid lumen 38. Rib 292 separates a flush chamber 326 (which is in communication with flush opening 266) and vacuum chamber 282.

A shaft mount 312 is received within inner mounting member 294. Shaft mount 312 is generally hollow. End cap 305 includes an aspiration mount 314 having an opening 316. The shaft mount 312 is disposed through opening 316. Shaft mount 312 is in fluid communication with proximal end 258 of shaft member 214, and in particular with aspiration lumen 36. Shaft mount 312 is configured to be connected to a suitable vacuum source. An outer surface of shaft mount 312 may include a mounting collar 317. Mounting collar 317 positions shaft mount 312 within inner mounting member 294, as well as allow for rotation of shaft mount 312 relative to end cap 305. A seal member 319 may be positioned around shaft mount 312, within a cavity 321 of end cap 305. Seal member 319 serves to direct aspiration to aspiration lumen 36. Area 323, adjacent to stabilizing member 301, is filled with adhesive (not shown) or other suitable material so ensure that aspiration is directed to aspiration lumen 36. Further, to isolate fluid delivery from aspiration, areas 325 and 327 are filled with adhesive on either side of a fluid channel 329 formed in inner mounting member 294 that is in communication with one of openings 284 and irrigation opening 265, similar to what is shown and described in FIG. 7B.

Flush chamber 326 is provided between rib 292 and radially extending edge 303 of inner mounting member 294. Flush chamber 326 is in communication with one of the openings 284 through sleeve 262, as well as flush opening 266 that is formed within shaft member 214. Flush opening 266 is in communication with fluid lumen 38. In one embodiment and may be sized to provide a controlled flow rate of fluid through the fluid lumen 38.

Control valve 228 comprises vent opening 226 and slidable sleeve 232. Vent opening 226 is in communication with vacuum chamber 282. Slidable sleeve 232 is configured to be selectively moved to cover or uncover vent opening 226 to immediately vary aspiration being delivered through aspiration lumen 36. More specifically, in the arrangement depicted in FIG. 10A, when it is desired to have full aspiration, slidable sleeve 232 is moved distally to completely cover vent opening 226. When it is desired to reduce aspiration pressure, slidable sleeve 232 is moved in a proximal direction to at least partially expose vent opening 226, thereby venting vacuum chamber 282. When slidable sleeve 232 is moved so as to completely expose vent opening 226, there is no aspiration being delivered to aspiration lumen 36. This configuration is advantageous in that it permits a user to immediately release tissue while in use, as well as reduce aspiration as needed. Due to its position on handpiece 212, slidable sleeve 232 is easy to manipulate with a single hand from any orientation of the user gripping the device, also providing improved ease of use.

In one exemplary arrangement, vent opening 226 has a teardrop shape. This shape permits a controlled reduction of aspiration as slidable sleeve 232 moves proximally. However, it is understood that other shapes of vent opening 226 may be employed.

An alternative arrangement for control valve 228' is shown in FIG. 13. Control valve 228' also comprises slidable sleeve 232 and vent opening 226. In this arrangement, however, slidable sleeve 232 is either biased toward distal end 276 of sleeve 262 with a spring mechanism (such as that shown in phantom in FIG. 10A) or permitted to freely float over sleeve 262. When permitted to freely float, as surgical device 200' is used distal end 276 will be oriented in a downward direction, slidable sleeve 262 will automatically slide toward the distal end 276. This action will completely uncover vent opening 226, thereby ensuring that no vacuum is delivered.

However, when vacuum is desired to be delivered to the distal end 276, the slidable sleeve 232 is moved in a proximal direction. In the control valve 228', the vent opening 226 is oriented so that the widest part of the teardrop shape is oriented toward the distal end 276 such that as slidable sleeve 232 is moved over the vent opening 226, the widest part will be covered first.

As outer member 264 is not required, a stiffening member 215 may be provided. In one exemplary arrangement, stiffening member 215 may extend substantially the length of the shaft member 214. More specifically, stiffening member 215 may be disposed in fluid lumen 38, as illustrated in FIG. 11. Stiffening member 215 assists in enabling the shaft member 214 to hold its shape.

As a further alternative, the electrodes 216 may be annealed. Annealing the electrodes 216 will assist in enabling the shaft member 214 to hold its shape. Further, annealing will also permit the user to selectively shape the shaft member 214, and once formed, for that shape to be maintained. While the electrodes 216 may be annealed throughout its length, it is also contemplated that the electrodes 216 are only selectively annealed toward the distal aspect, i.e., those portions of the electrodes 216 that are disposed within the shaft member 214, but distal of the cap member 260.

Referring to FIGS. 9A and 9B, the proximal end 258 of shaft member 214 is configured with a land area 320 having grooves 322 formed in a top surface thereof. Grooves 322 extend into an end face 324 of shaft member 214 and join fluid openings 44 (or 144, 544, 644). Electrodes 216 are configured to be received within fluid openings 44.

In operation, fluid is delivered into opening 284 (via a fluid tubing connected thereto) and communicated into fluid channel 329 so as to direct irrigation to electrode channels 40. In this manner, fluid exits around electrodes 16, 116, 216, 316, 416, 516, 616, 674 during operation, so as to provide metered irrigation to the surgical site, thereby creating a "wet field". Fluid may further be selectively provided to the surgical field through the other opening 284 (via a fluid tubing connected thereto). The other opening 284 is in communication with a flush chamber 326. A flush opening 266 formed in fluid lumen 38 is arranged within the flush chamber 326. In this manner, additional fluid may be optionally delivered through fluid lumen 38 to power flush a surgical site, thereby enabling clearing of surgical site, as well as assisting in locating the source of bleeding.

Referring to FIG. 13, as discussed above, proximal end 277' of sleeve 262' includes a hub 263', which include fluid openings 288. Fluid tubes 291*a* and 291*b* may be directly fixedly secured to fluid openings 288. As is shown in FIG. 10B, one of fluid tubes 291*a* is operatively connected to flush chamber 326 via flush opening 266, while the other of fluid tubes 291*b* is operatively connected to fluid channel 329 so as to direct irrigation to fluid lumen 38.

An end cap 305' slides over a proximal end of hub 263' until end cap 305' is positioned adjacent fluid openings 288. End cap 305' is configured with an outer sleeve portion 402 that is generally the same diameter as sleeve 262'. Instead of laterally spaced extension members 306 on hub 263, end cap 305' is provided with a fluid retention member 404. Fluid retention member 404 includes an opening therethrough 406 that is sized to receive fluid tubes 291*a*, and 291*b* therein. An opening is formed in the proximal end of end cap 305', similar to that depicted in FIG. 10B. The opening is configured to be connected to an aspiration tubing 408 to deliver vacuum to vacuum chamber 282 via aspiration lumen 36.

End cap 305' further includes a connection mount 290' disposed on the proximal end of end cap 305'. The connection mount 290' may be integrally formed with end cap 305' and is configured to receive a connection port 410 to operatively connect electrodes 216 to an electrical source for energizing electrodes 216.

A further alternative arrangement for a bipolar surgical device 500 is shown in FIGS. 14A-14B. Bipolar surgical device 500 is similar to devices 10 and 200 in that it includes a handpiece 512, a shaft member 514 extending distally from handpiece 512 and electrodes 16, 116, 216, 316, 416, 516, 616, 674 (as best seen in FIGS. 2A-2N) extending distally from shaft member 514. Operatively connected to handpiece 512 is an aspiration line 518 and a cautery supply cable 522.

In this embodiment, however, a single fluid delivery line 520 is operatively connected to the handpiece 512. Fluid delivery line 520 has a distal end 522 that is secured to a fluid opening 584 and a proximal end 524 that is connected to a connector element 526. Connector element 524 includes two inlets 528*a* and 528*b* and a single outlet 530. Proximal end 524 of fluid delivery line 520 is fixedly attached to outlet 530.

Connected to inlet 528*a* is fluid line 591*a*. An opposite end of fluid line 591*a* may be connected to a one-way check valve 532. A second fluid line 593*a* is connected to check valve 532. Second fluid line 593*a* terminates in a fitting 534. Fitting 534 is configured to be connected to a fluid source. In operation, once a fluid source is connected to the fitting 534, fluid is delivered through check valve 532, into fluid line 591*a*, through connector 526 and into fluid delivery line 520. Fluid is then fed into electrode channels 40, 240 so as to exit shaft member 514 adjacent the electrodes tips. This configuration allows continuous delivery or irrigation of fluid at a surgical site so as to create a wet surgical field. Because the check valve 532 is a one-way check valve, fluid is prevented from back flushing through the check valve 532.

Connected to inlet 528*b* is another fluid line 591*b*. Fluid line 591*b* terminates in a fitting 536. Fitting 536 is also configured to be connected to a secondary fluid source. When fitting 536 is connected to the secondary fluid source, fluid is delivered through fluid line 591*b*, through connector 526 and into fluid delivery line 520. Fluid is then fed into electrode channels 40, 240 so as to exit shaft member 214 adjacent the electrode tips. However, the secondary fluid source is configured to selectively deliver a burst of fluid, so as to power flush the surgical site. Power flushing the surgical site in operation is beneficial to clear the surgical field and locate bleeding sources in the surgical field.

The arrangement in FIGS. 14A and 14B differs from the arrangement shown in FIGS. 10A and 10B in that only a lumen is provided in shaft member 514 of surgical device 500 as opposed to fluid lumen 38 and electrode channels 40 provided in shaft member 214. More specifically, in the arrangement of surgical device 500 two sources of irrigation are delivered through electrode channels 40 to provided constant irrigation at the surgical site, as well as provide a selective power flush through the same electrode channels 40. This configuration thereby allows a reduced diameter shaft 514, thereby providing improved visualization capability at the surgical site.

Figure 15A:
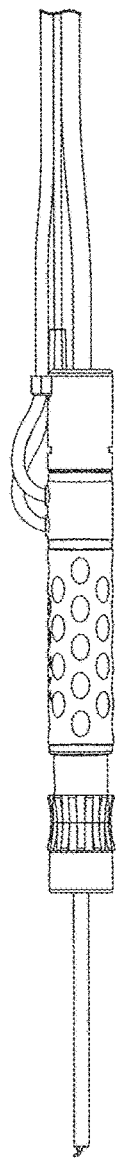
FIGS. 15A-15C are elevational views of a bipolar instrument, illustrating various cannula lengths and configurations.
Figure 15B:
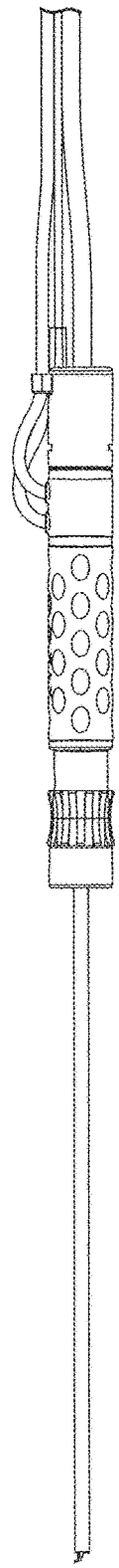
Figure 15C:
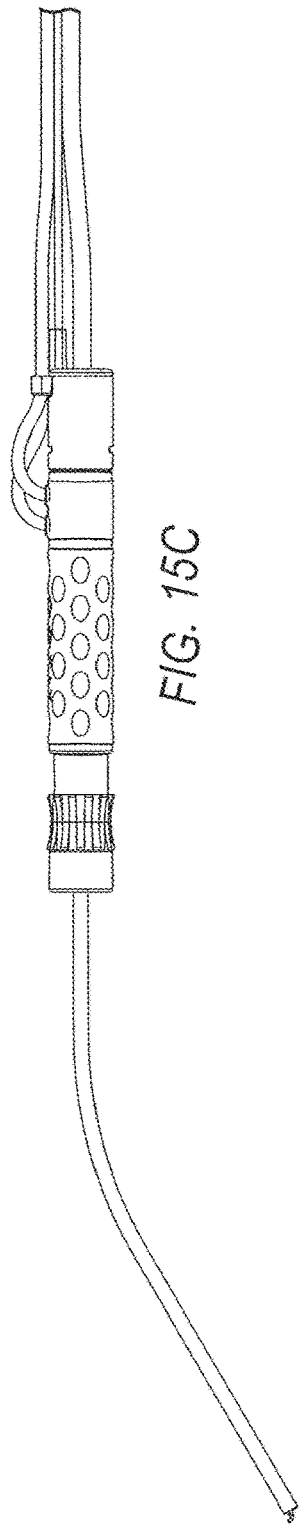

FIGS. 15A-15C illustrate different configurations for the length of shafts 514A, 514B, 514C. For example, FIG. 15A has a relatively short length, as compared to the arrangement shown in FIG. 15B. In the arrangement shown in FIG. 15B, the increase length of shaft member 514B may be advantageous for surgical areas that are seated deeply within the body. As illustrated in FIG. 15C, the shaft member 514C may be configured to be somewhat flexible so as to allow a user to custom bend the shaft member 514C.

Figure 16A:
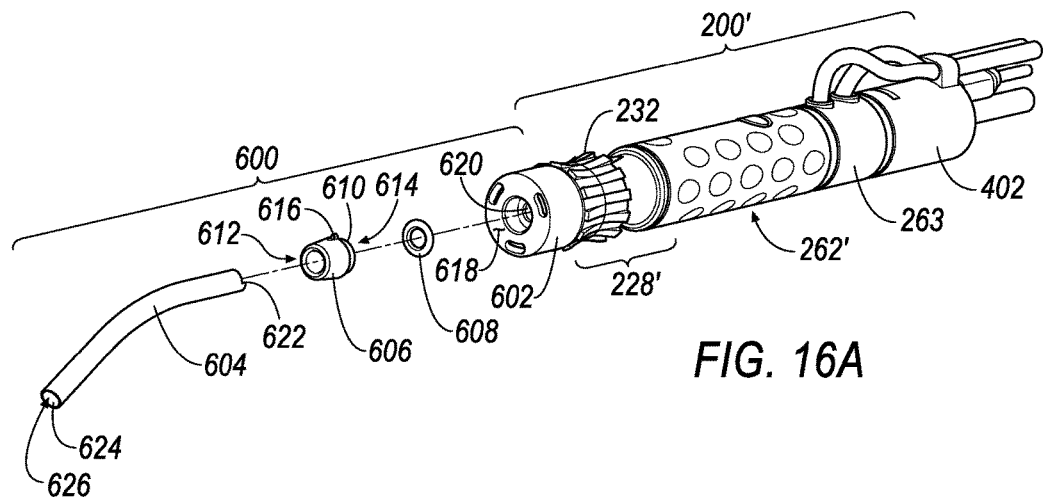
FIG. 16A is a partially exploded view of a stiffening adapter for use with a bipolar instrument.
Figure 16B:
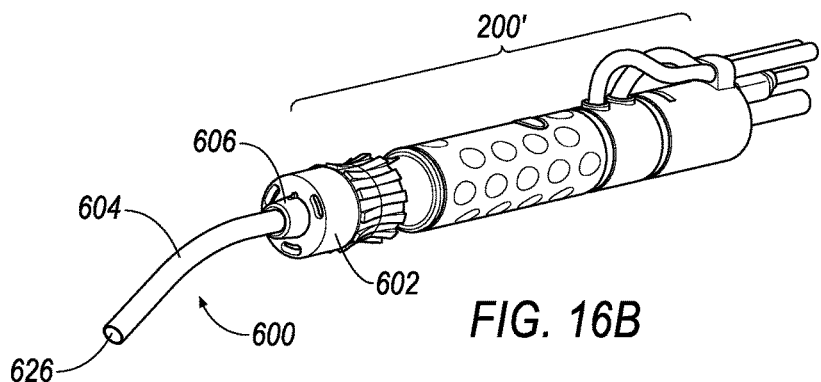
FIG. 16B is a perspective view of the stiffening adapter of FIG. 16A attached to the bipolar instrument.
Figure 16C:
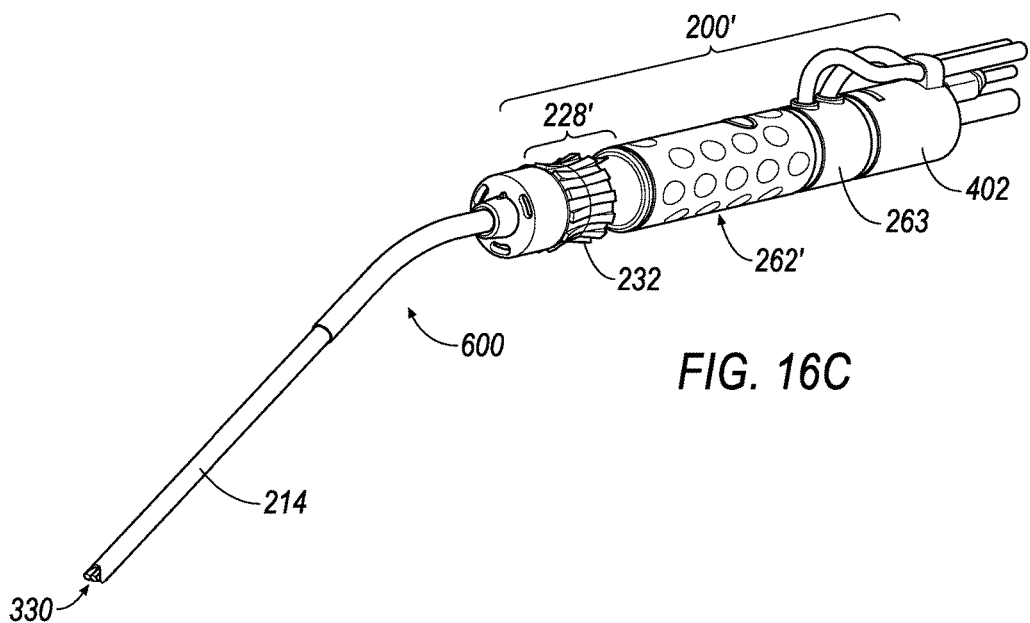
FIG. 16C is a perspective view of the stiffening adapter of FIGS. 16A-16C and its relationship with a sleeve of the bipolar instrument.

Referring to FIGS. 16A-16B, an optional stiffening adapter 600 is illustrated that may be attached to a surgical device. While surgical device 200' is depicted in FIGS. 16A-16B, it is understood that stiffening adapter 600 may be used with other embodiments described herein, as well as other surgical devices.

Stiffening adapter 600 comprises cap member 602, stiffening sleeve 604, a sleeve retainer 606 and a seal member 608. The seal member 608 is positioned about a seal mount 610 formed on a proximal end of the sleeve retainer 606. The seal member 608 is sized to have an inner diameter that is normally smaller than an outside diameter of the sleeve mount 610. When positioned on the seal mount, the inner diameter of the seal member 608 enlarges so as to frictionally engage the seal mount 610.

The sleeve retainer 606 has distal 612 and proximal openings 614 and may be tapered such that the distal end is smaller than the proximal end. A locking tab 616 may be formed on an outside surface of the sleeve retainer 606. The sleeve retainer 606 is positioned within the cap member 602 (as is the seal member 608). In one exemplary arrangement, a portion of the sleeve retainer 606 extends distally outwardly from a distal face 618 of the cap member 602.

The cap member 602 is open on the proximal end so as to partially receive a distal end face of the surgical device 200', similar to body member 267. The cap member 602 further defines a channel mount 620 into which the sleeve retainer 606 is positioned. In one exemplary arrangement, the locking tab 616 may cooperate with a locking detent (not shown)

formed in the channel mount 620 so as to lock the sleeve retainer 606 to the cap member 602, such as in a snap-fit arrangement.

The stiffening sleeve 604 is defined by a proximal end 622 and a distal end 624. The proximal end 622 is mounted within the sleeve retainer 606. The stiffening sleeve 604 includes a channel 626 that extends between the proximal and distal ends 622 and 624. The diameter of the channel 626 is sized to be slightly larger than a cross-section dimension of shaft member 214. The stiffening sleeve is constructed of a material that is more rigid than the shaft member 214. One example of a suitable material is stainless steel, though it is contemplated that other suitable materials may also be used.

In one exemplary arrangement the material for the stiffening sleeve may have a degree of malleability that allows a user to impart a bending force to achieve a desired bend in the stiffening sleeve. Once bent, the stiffening sleeve will retain the shape of the bend once the bending force is removed. Alternatively, the stiffening sleeve may be provided with a bend preformed. Providing a bend to direct the distal end 303 of the surgical device 200' away from a longitudinal axis of the surgical device 200' advantageously improves a line of sight for using the surgical device. This is especially true if the surgical device 202' is used in a delivery cannula, such as that disclosed in commonly owned U.S. patent application Ser. No. 13/444,713, the contents of which are incorporated by reference in its entirety.

The stiffening sleeve 604 may also be provided with an anti-reflective surface. In one exemplary arrangement, the anti-reflective surface may be formed by texturing the outer surface of the stiffening sleeve 604. The anti-reflective surface serves to prevent glare from illumination sources, thereby reducing eye fatigue during use of the surgical device 200'.

The cap member 602 is attached to the distal end of the surgical device 200'. In one exemplary arrangement, the cap member 602 is fixedly attached such that the stiffening adapter 600 is permanently attached to the distal end of the surgical device 200.' The fixed attachment may be accomplished by a variety of different mechanisms. Examples include, but are not limited to using glue, ultrasonic welding and/or a snap-fit arrangement.

Alternatively, the stiffening adapter 600 may be configured to be selectively detachable. For example, the cap member 602 may be threadingly engaged with the distal end of the surgical device 200'. In such an example, the interior of the cap member 602, as well as a portion of the outer surface of the distal end of the surgical device 200' would need to include corresponding threads. Other suitable methods of selectively attaching the stiffening adapter 600 to the surgical device 200' include using a keyed connection or other mechanical attachment mechanism.

It will be appreciated that the surgical instrument and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A surgical device, comprising:
    a housing;
    a shaft member at least partially disposed within the housing, the shaft member including a pair of electrode channels that open at a distal end of the shaft member, wherein the pair of electrode channels are positioned adjacent to one another;
    a pair of electrodes configured to deliver energy, wherein each of the pair of electrodes are configured to be disposed in each of the pair of electrode channels such that distal ends of each of the pair of electrodes are arranged to protrude from the distal end of the shaft member;
    wherein the housing further comprises a vacuum chamber therein, wherein the shaft member extends through the vacuum chamber and the shaft member includes a vacuum opening that is in communication with the vacuum chamber to deliver vacuum from the vacuum chamber through an aspiration lumen of the shaft to at least one aspiration lumen opening at the distal end of the shaft member; and
    a stiffening adapter having a stiffening sleeve, wherein the stiffening adapter is attached to a distal end of the housing;
    wherein the shaft member extends distally from a distal end of the stiffening sleeve.

2. The surgical device of claim 1, wherein the shaft member is selectively formable by a user.

3. The surgical device of claim 1, wherein the stiffening adapter is permanently attached to the distal end of the housing.

4. The surgical device of claim 3, wherein the stiffening adapter is glued to the distal end of the housing.

5. The surgical device of claim 3, wherein the stiffening adapter is ultrasonically welded to the distal end of the housing.

6. The surgical device of claim 1, wherein the stiffening adapter is selectively attached to the distal end of the housing.

7. The surgical device of claim 6, wherein the stiffening adapter is threadingly engaged with the distal end of the housing.

8. The surgical device of claim 1, wherein the stiffening sleeve has a preformed bend.

9. The surgical device of claim 1, wherein the stiffening sleeve is selectively formable to a desired bend.

10. The surgical device of claim 1, wherein the stiffening sleeve has an anti-reflective outer surface.

11. The surgical device of claim 3, wherein an outer surface of the stiffening sleeve is textured to create an anti-reflective outer surface.

12. The surgical device of claim 1, wherein the stiffening adapter further comprises a cap member and a sleeve retainer, wherein the sleeve retainer is positioned within the cap member and a proximal member is secured within the sleeve retainer.

13. The surgical device of claim 12, wherein the sleeve retainer further comprises a locking member that cooperates with a corresponding locking member formed on the cap member to secure the sleeve retainer within the cap member.

14. The surgical device of claim 12, wherein the sleeve retainer is tapered outwardly from a distal end to a proximal end of the sleeve retainer.

15. The surgical device of claim 12, wherein the sleeve retainer further comprises a seal mount positioned on a proximal end of the sleeve retainer and a seal member that is configured to be mounted to the seal mount.

\* \* \* \* \*